(12) United States Patent
Suga et al.

(10) Patent No.: US 9,000,190 B2
(45) Date of Patent: Apr. 7, 2015

(54) AMIDE COMPOUND OR SALT THEREOF, BIOFILM INHIBITOR, BIOFILM REMOVER AND DISINFECTANT CONTAINING THE SAME

(71) Applicants: The University of Tokyo, Bunkyo-ku, Tokyo (JP); Otsuka Chemical Co., Ltd., Osaka-shi, Osaka (JP)

(72) Inventors: Hiroaki Suga, Tokyo (JP); Jun Igarashi, Tokushima (JP)

(73) Assignees: University of Tokyo, Tokyo (JP); Otsuka Chemical Co., Ltd., Osaka (JP)

( * ) Notice: Subject to any disclaimer, the term of this patent is extended or adjusted under 35 U.S.C. 154(b) by 0 days.

(21) Appl. No.: 14/264,471

(22) Filed: Apr. 29, 2014

(65) Prior Publication Data
US 2015/0018564 A1    Jan. 15, 2015

Related U.S. Application Data

(62) Division of application No. 13/567,695, filed on Aug. 6, 2012, now Pat. No. 8,748,617, and a division of application No. 11/935,512, filed on Nov. 6, 2007, now Pat. No. 8,258,307.

(60) Provisional application No. 60/857,172, filed on Nov. 7, 2006.

(51) Int. Cl.
| | | |
|---|---|---|
| C07D 295/22 | (2006.01) | |
| A61K 31/40 | (2006.01) | |
| C07D 207/50 | (2006.01) | |
| A01N 43/36 | (2006.01) | |
| A61K 8/49 | (2006.01) | |
| A61Q 11/00 | (2006.01) | |

(52) U.S. Cl.
CPC .............. *C07D 207/50* (2013.01); *A01N 43/36* (2013.01); *A61K 8/4913* (2013.01); *A61Q 11/00* (2013.01)

(58) Field of Classification Search
CPC .................................................. C07D 207/14
USPC .......................................... 548/557; 514/426
See application file for complete search history.

(56) References Cited

U.S. PATENT DOCUMENTS

| | | |
|---|---|---|
| 4,310,547 A | 1/1982 | Hunt et al. |
| 5,817,599 A | 10/1998 | Iida et al. |

FOREIGN PATENT DOCUMENTS

| | | |
|---|---|---|
| JP | 2004-528356 A | 9/2004 |
| WO | 96/26747 A2 | 9/1996 |
| WO | 99/06387 A2 | 2/1999 |
| WO | 02/088298 A1 | 11/2002 |
| WO | 2004/016213 A2 | 2/2004 |
| WO | 2004/099175 A2 | 11/2004 |

OTHER PUBLICATIONS

L. McLaughlin-Borlace et al., "Bacterial biofilm on contact lenses and lens storage cases in weaters with microbial keratitis", Journal of Applied Microbiology, vol. 84, 1998, pp. 827-838 [XP002618713].
Supplementary European Search Report dated Mar. 22, 2011, in corresponding European Application No. 07830633.9.
Manetti et al., "Design Synthesis, and Preliminary Pharmacological Evaluation of a Set of Small Molecules that Directly Activate Gi Proteins," Journal of Medicinal Chemistry, 2005, vol. 48, pp. 6491-6503.
A. Bennick, "Salivary proline-rich proteins", Molecular and Cellular Biochemistry (1982) vol. 45, pp. 83-99.
European Office Action issued in European Application No. 07830633.9, dated Sep. 10, 2013, (5pgs).

*Primary Examiner* — John Mabry
(74) *Attorney, Agent, or Firm* — Fitch, Even, Tabin & Flannery LLP

(57) ABSTRACT

The present invention provides a new amide compound and salt thereof that is capable of inhibiting biofilm formation or removing deposited biofilms. The present invention also provides a biofilm formation inhibitor or a biofilm remover containing the amide compound or salt thereof as an active ingredient.

An amide compound or salt thereof according to the present invention is denoted by General Formula (1):

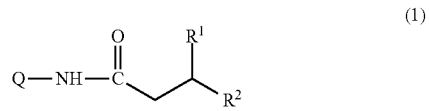

wherein $R^1$ is a hydrogen atom or a hydroxyl group, $R^2$ is a $C_{5-12}$ alkyl group, and Q is a substituent denoted by Formula (Q1) or (Q2),

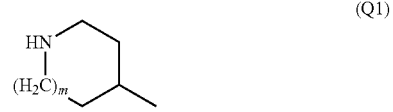

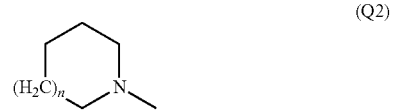

wherein n and m are 0 or 1.

12 Claims, 12 Drawing Sheets

Control

Compound 1a-1

Compound 1b-1

Compound 1c-1

Compound 1c-2

Comparative Compound 1

Comparative Compound 2

Comparative Compound 3

AMIDE COMPOUND OR SALT THEREOF, BIOFILM INHIBITOR, BIOFILM REMOVER AND DISINFECTANT CONTAINING THE SAME

CROSS REFERENCE TO RELATED APPLICATION

This application is a Divisional patent application of U.S. application Ser. No. 13/567,695, filed Aug. 6, 2012, which is a Divisional of Ser. No. 11/935,512, filed Nov. 6, 2007, which claims the priority from U.S. Provisional Application No. 60/857,172, filed Nov. 7, 2006, the complete disclosures of which are incorporated herein by reference.

TECHNICAL FIELD

The present invention relates to a new amide compound and salt thereof that is capable of inhibiting biofilm formation, stripping off or removing deposited biofilms, or disinfection. The present invention further relates to a biofilm formation inhibitor, a biofilm remover (biofilm stripping agent) and a disinfectant containing the amide compound or salt thereof as an active ingredient, and the usage thereof.

BACKGROUND ART

A certain kind of microorganism, such as bacteria or fungus, adheres to a carrier surface and forms a colony thereon. When the colony contains a certain number of *bacillus* cells, it forms/secretes an organic substance such as polysaccharide or glycoprotein that grows into a biofilm. A biofilm is akin to a medium that allows other microorganisms to enter and form a complicated microorganism group inside. Such biofilm deposits can be found everywhere in the natural environment, in industrial areas, and in humans. Such biofilm deposits cause numerous problems, including those in industrial facilities such as the erosion of metal tubing in factory drain pipes or malfunctions during valve operations, the generation of *Legionella* bacteria in circulating-type bathtubs, as well as various human infections including skin diseases such as pimples or skin inflammation, eye infections such as microbial keratitis via contact lenses, intraoral diseases such as caries or periodontitis, or other diseases such as otitis media, bacterial prostatitis, or cystic fibrosis pneumonia.

Many of these infections caused by biofilms (biofilm infection), for example, periodontitis, are intractable, and one reason for the intractableness is that the microorganisms in a biofilm are covered by a film (an extracellular matrix), and will therefore not directly come into contact with immune system cells or antibacterial substances. Another reason is that bacterias in a biofilm have very slow metabolisms, which is also thought to interfere with antibiotics, which show the greatest effect in actively-dividing cells. For the reasons above, in order to completely cure biofilm infections, it is necessary to ensure both the prevention of biofilm deposits by microorganisms as well as the removal of deposited biofilms.

Biofilms are generally removed physically, for example, by scraping them off with a brush, etc. However, because biofilms generally adhere tightly to a carrier surface, this is not particularly effective, even with a great deal of effort.

In light of such existing problems, compounds that can control the deposit of biofilms have been attracting attention. For example, Patent Documents 1 and 2 disclose the invention of a compound having a certain amide structure effective in the control of biofilm deposition.

Patent Document 1: WO2004/016213
Patent Document 2: WO2002/088298

DISCLOSURE OF INVENTION

However, the compounds disclosed in Patent Documents 1 and 2 are not capable of stripping off or removing biofilms already formed. The suppression or inhibition of biofilm formation or deposition may reduce the thickness of the formed or deposited biofilms to some extent, or may even destroy the film if the compounds exhibit desired effect. However, since the microorganisms in the film are still alive, there is the possibility that the microorganisms may form a biofilm again when the effect of the antibacterial agent diminishes or disappears. In view of this, this technology is not an ultimate solution for various biofilm defects such as infections. Therefore, such a drug for inhibiting biofilm formation or deposition is not sufficient to correct the various defects caused by biofilms, or to completely cure biofilm infections. For this reason, there has been demand for a drug that can strip off or remove a deposited biofilm.

An object of the present invention is to provide a compound serving to strip off or remove deposited biofilms, particularly to a new compound serving both to inhibit biofilm formation by microorganisms and to strip off or remove deposited biofilms. The present invention also provides a biofilm remover (including stripping agent) and a biofilm formation inhibitor containing the compound as an active ingredient, particularly to a biofilm remover and a biofilm formation inhibitor having a certain effect on biofilms formed by bacterias such as *Pseudomonas aeruginosa* or periodontitis pathogenic bacteria. The present invention further provides a disinfectant containing the compound as an active ingredient. The present invention further provides product containing the biofilm remover, the biofilm formation inhibitor or the disinfectant, such as an oral composition to prevent or treat intraoral diseases such as periodontitis related to periodontitis pathogenic bacteria.

As a result of intensive studies, the inventors of the present invention have found that a compound having a certain amide structure has the effect of both stripping off or removing deposited biofilms and inhibiting biofilm formation by microorganisms. The inventors also found that the amide compound has disinfecting activity comparative to that of existing antibiotics. Because of this characteristic of the compound, the inventors were able to complete the present invention.

The following (I) to (V) are included in the scope of the present invention.

(I) New Amide Compound or Salt Thereof (I-1). An amide compound denoted by General Formula (1) or salt thereof:

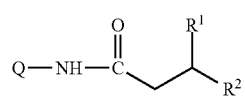
(1)

wherein $R^1$ is a hydrogen atom or a hydroxyl group, $R^2$ is a $C_{5-12}$ alkyl group, and Q is a substituent denoted by Formula (Q1) or (Q2).

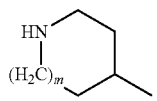

(Q1)

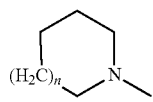

(Q2)

wherein n and m are 0 or 1.

(I-2). An amide compound or salt thereof according to (I-1), wherein, in General Formula (1), Q is a substituent denoted by Formula (Q1) wherein m is 0.

(I-3). An amide compound or salt thereof according to (I-1), wherein, in General Formula (1), Q is a substituent denoted by Formula (Q1) wherein m is 1.

(I-4). An amide compound or salt thereof according to (I-1), wherein, in General Formula (1), Q is a substituent denoted by Formula (Q2) wherein n is 0.

(I-5). An amide compound or salt thereof according to (I-1), wherein, in General Formula (1), Q is a substituent denoted by Formula (Q2) wherein n is 1.

(I-6). An amide compound or salt thereof according to (I-1), wherein the amide compound denoted by General Formula (1) is at least one compound selected from the group consisting of:
N-(pyrrolidin-3-yl) decanoyl amide,
N-(pyrrolidin-3-yl) dodecanoyl amide,
N-(pyrrolidin-4-yl) decanoyl amide,
N-(pyrrolidin-4-yl) dodecanoyl amide,
N-(pyrrolidin-1-yl) dodecanoyl amide,
N-(pyrrolidin-1-yl)-3-hydroxy dodecanoyl amide,
N-(piperidine-1-yl) dodecanoyl amide.

(II) Biofilm Remover (Biofilm Stripping Agent)

(II-1). A biofilm remover containing the amide compound or salt thereof according to any one of (I-1) through (I-6), as an active ingredient.

(II-2). A biofilm remover according to (II-1), wherein the biofilm remover removes biofilms formed by *Pseudomonas aeruginosa* or periodontitis pathogenic bacteria.

(II-3). Use of the amide compound or salt thereof according to any one of (I-1) through (I-6) as a biofilm remover.

(II-4). Use of the amide compound or salt thereof according to any one of (I-1) through (I-6) for preparation of a biofilm remover.

(II-5). An amide compound or salt thereof according to any one of (I-1) through (I-6) used as an active ingredient of a biofilm remover.

(III) Biofilm Formation Inhibitor (III-1). A biofilm formation inhibitor containing the amide compound or salt thereof according to any one of (I-1) through (I-6), as an active ingredient.

(III-2). A biofilm formation inhibitor according to (III-1), wherein the biofilm formation inhibitor inhibits formation of biofilms formed by *Pseudomonas aeruginosa* or periodontitis pathogenic bacteria.

(III-3). Use of the amide compound or salt thereof according to any one of (I-1) through (I-6), as a biofilm formation inhibitor.

(III-4). Use of the amide compound or salt thereof according to any one of (I-1) through (I-6) for preparation of a biofilm formation inhibitor.

(III-5). An amide compound or salt thereof according to any one of (I-1) through (I-6) used as an active ingredient of a biofilm formation inhibitor.

(IV) Disinfectant (IV-1). A disinfectant containing the amide compound or salt thereof according to any one of (I-1) through (I-6), as an active ingredient.

(IV-2). A disinfectant containing the amide compound or salt thereof according to (I-2) or (I-3), as an active ingredient.

(IV-3). A disinfectant according to (IV-1), wherein the amide compound is at least one compound selected from the group consisting of:
N-(pyrrolidin-3-yl) decanoyl amide,
N-(pyrrolidin-3-yl) dodecanoyl amide,
N-(pyrrolidin-4-yl) decanoyl amide, and
N-(pyrrolidin-4-yl) dodecanoyl amide.

(IV-4). Use of the amide compound or salt thereof according to any one of (I-1) through (I-6), preferably (I-2) or (I-3), as a disinfectant.

(IV-5). Use of the amide compound or salt thereof according to any one of (I-1) through (I-6), preferably (I-2) or (I-3), for preparation of a disinfectant.

(IV-6). An amide compound or salt thereof according to any one of (I-1) through (I-6), preferably (I-2) or (I-3), used as an active ingredient of a disinfectant.

(V) Usage of a Biofilm Remover, a Biofilm Formation Inhibitor or a Disinfectant (V-1). An oral composition containing the biofilm remover according to (II-2) for stripping off or removing biofilms formed by periodontitis pathogenic bacteria, the biofilm formation inhibitor according to (III-2) for inhibiting biofilms formed by periodontitis pathogenic bacteria, or the disinfectant according to (IV-1).

(V-2). An oral composition according to (V-1), for preventing or relieving intraoral diseases or oral odor caused by periodontitis pathogenic bacteria.

(V-3). Use of the biofilm remover according to (II-2) for stripping off or removing biofilm formed by periodontitis pathogenic bacteria, the biofilm formation inhibitor according to (III-2) for inhibiting formation of biofilms formed by or periodontitis pathogenic bacteria, or the disinfectant according to (IV-1), for preparation of an oral composition.

(V-4). Use according to (V-3), wherein the oral composition prevents or relieves intraoral diseases or oral odor caused by periodontitis pathogenic bacteria.

(V-5). A biofilm remover according to (II-2) for stripping off or removing biofilms formed by periodontitis pathogenic bacteria, a biofilm formation inhibitor according to (III-2) for inhibiting formation of biofilms formed by or periodontitis pathogenic bacteria, or the disinfectant according to (IV-1), used as an active ingredient of a oral composition.

(V-6). A biofilm remover according to (V-5), wherein the oral composition is an oral composition for preventing or relieving intraoral diseases or oral odor caused by periodontitis pathogenic bacteria.

and the state of biofilm formation when using a control test liquid (control) (Experiment Example 1).

Figure 3:
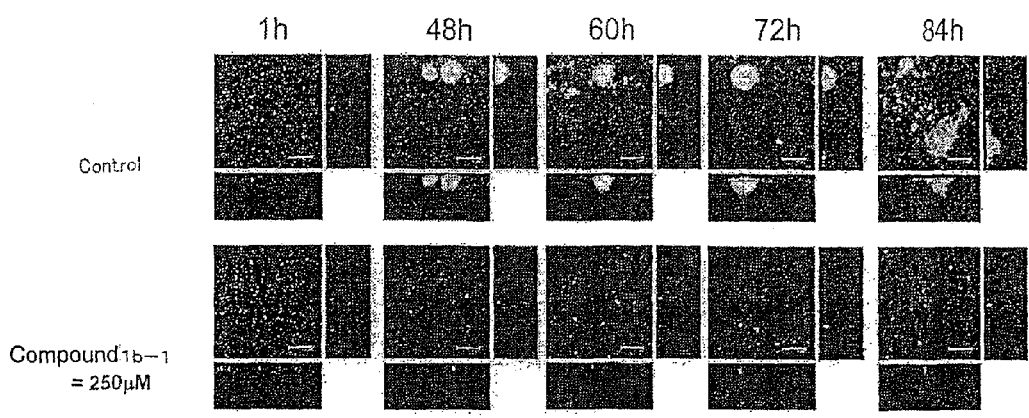

FIG. 3 shows a comparison between the state of biofilm ft/Elation when using a test liquid (Compound 1b-1, 250 μM) and the state of biofilm formation when using a control test liquid (control) (Experiment Example 1).

Figure 4:
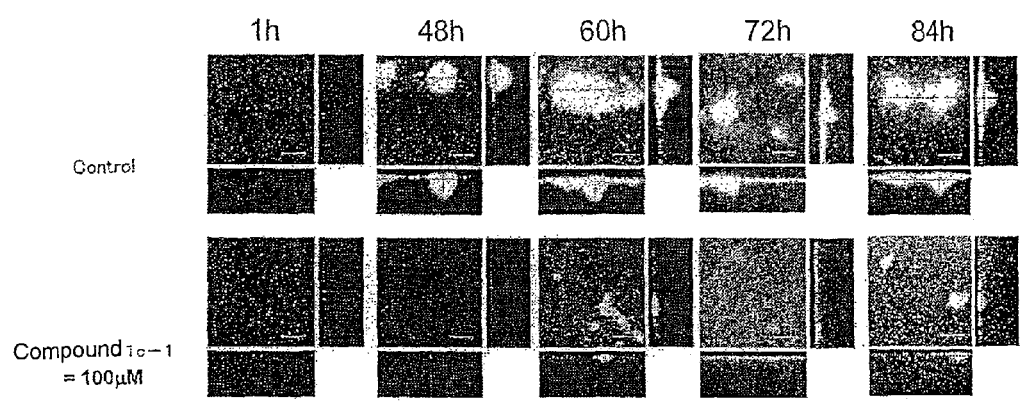

FIG. 4 shows a comparison between the state of biofilm formation when using a test liquid (Compound 1c-1, 100 μM) and the state of biofilm formation when using a control test liquid (control) (Experiment Example 1).

Figure 5:
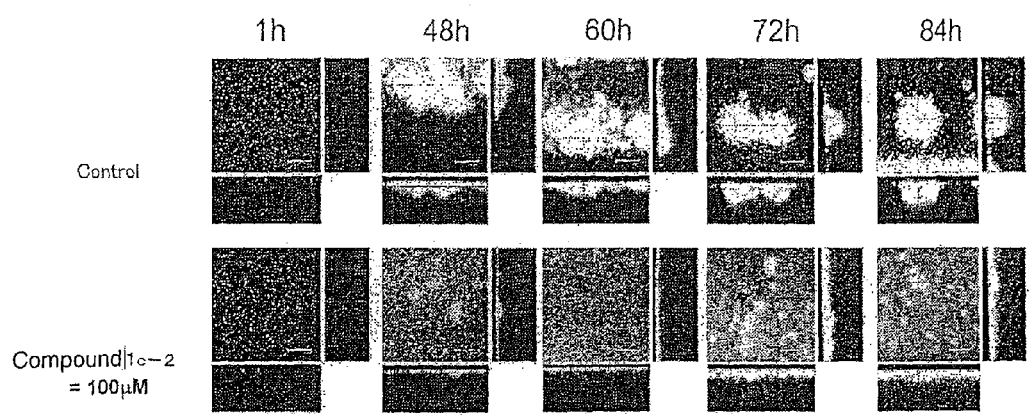

FIG. 5 shows a comparison between the state of biofilm formation when using a test liquid (Compound 1c-2, 100 μM) and the state of biofilm formation when using a control test liquid (control) (Experiment Example 1).

Figure 6:
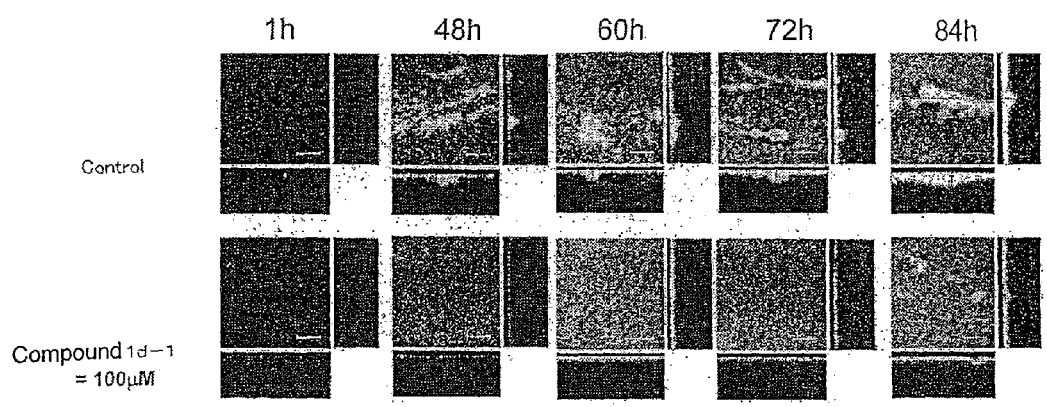

FIG. 6 shows a comparison between the state of biofilm formation when using a test liquid (Compound 1d-1, 100 μM) and the state of biofilm formation when using a control test liquid (control) (Experiment Example 1).

Figure 7:
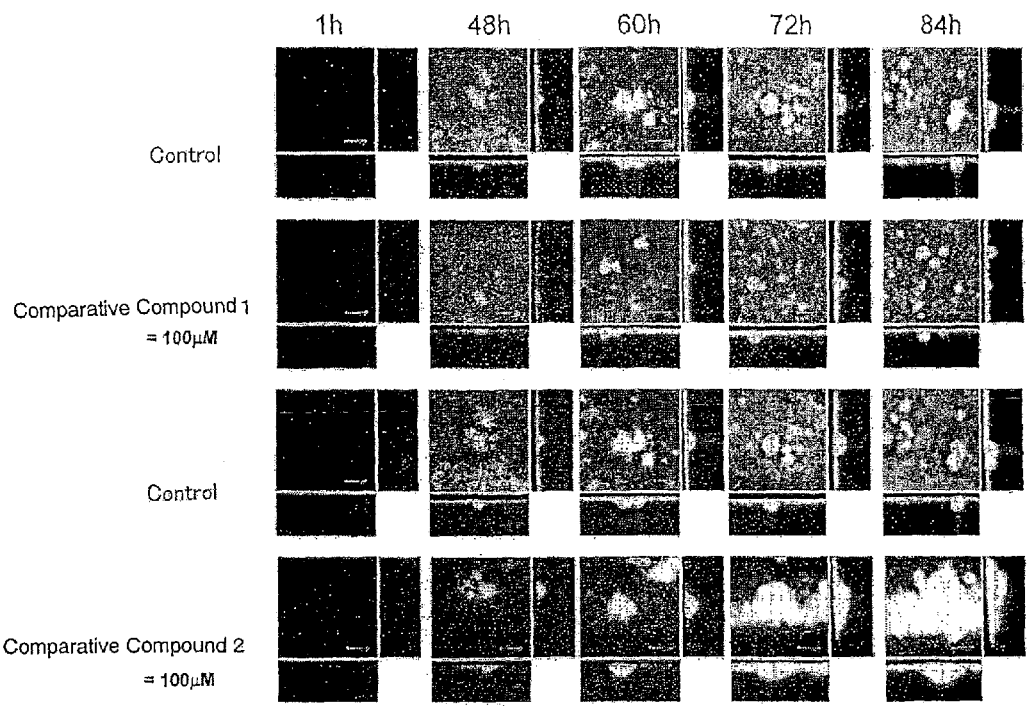

FIG. 7 shows a comparison between the state of biofilm formation when using a test liquid (Comparative Compounds 1 and 2, 100 μM) and the state of biofilm formation when of using a control test liquid (control) (Experiment Example 1).

Figure 8:
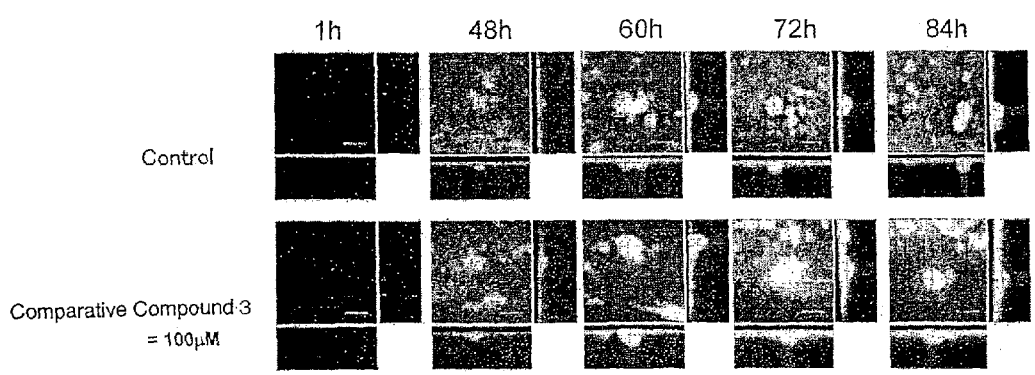

FIG. 8 shows a comparison between the state of biofilm formation when using a test liquid (Comparative Compound 3, 100 μM) and the state of biofilm formation when using a control test liquid (control) (Experiment Example 1).

Figure 9:
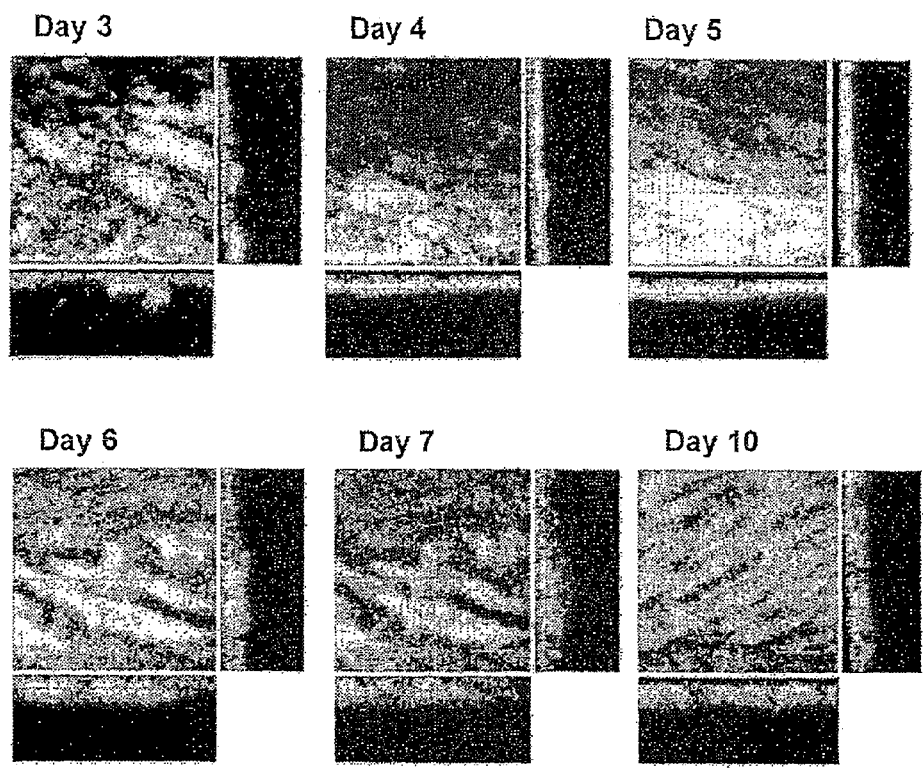

FIG. 9 shows the state of biofilm removal when using a control test liquid (Experiment Example 3).

Figure 10:
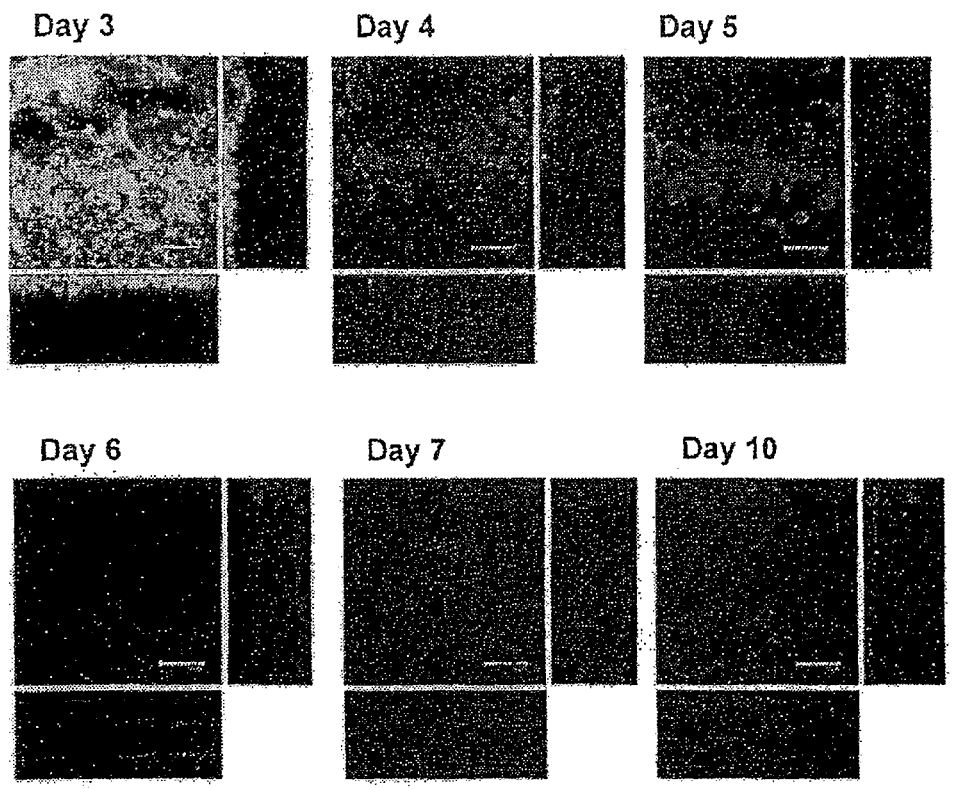

FIG. 10 shows the state of biofilm removal when using a test liquid (Compound 1a-1, 100 μM) (Experiment Example 3).

Figure 11:
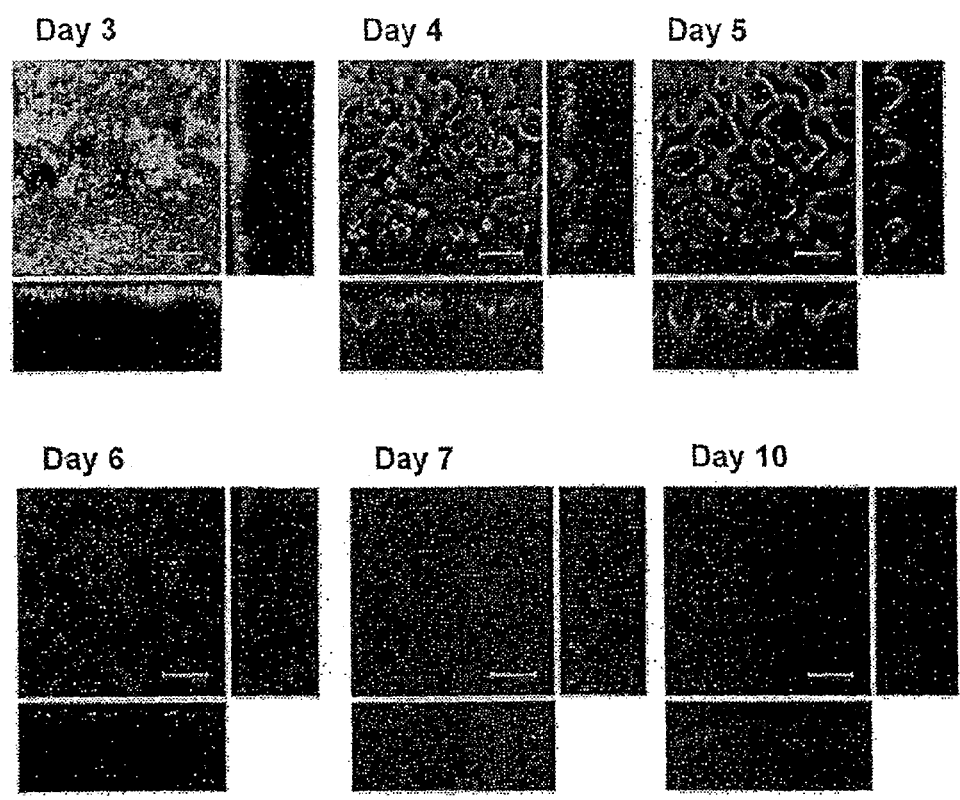

FIG. 11 shows the state of biofilm removal when using a test liquid (Compound 1b-1, 100 μM) (Experiment Example 3).

Figure 12:
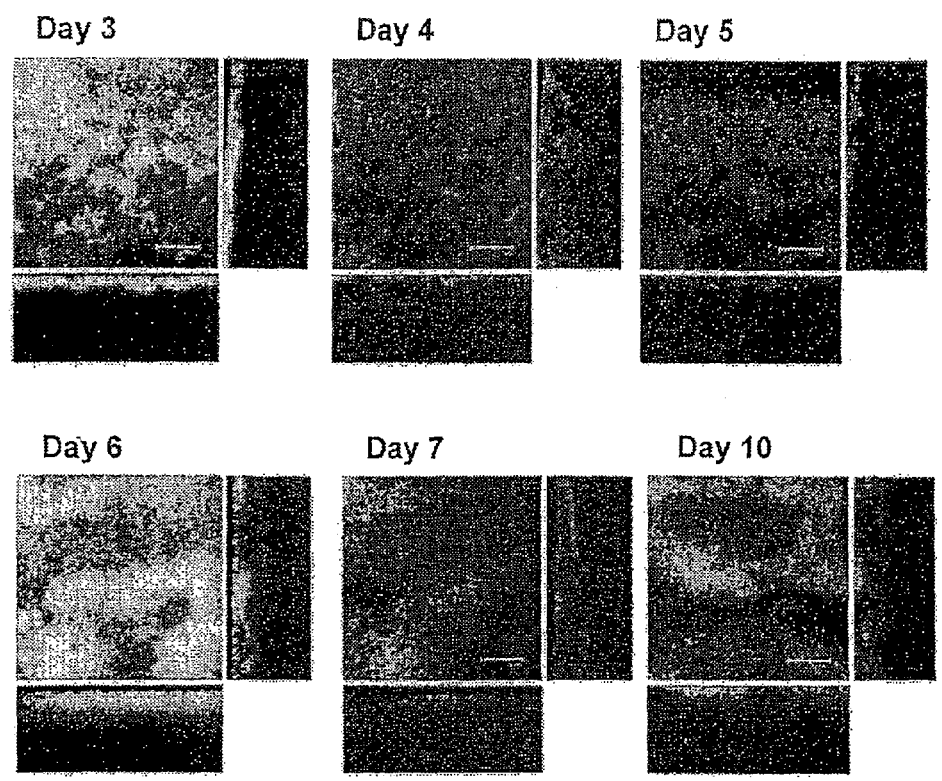

FIG. 12 shows the state of biofilm removal when using a test liquid (Compound 1c-1, 100 μM) (Experiment Example 3).

Figure 13:
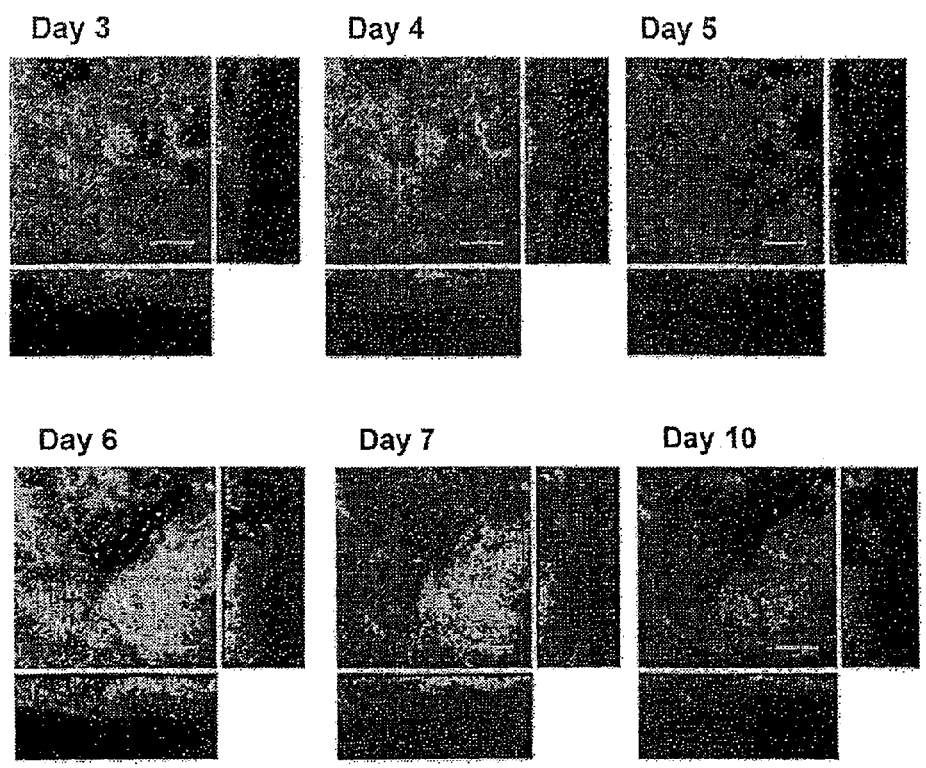

FIG. 13 shows the state of biofilm removal when using a test liquid (Compound 1c-2, 100 μM) (Experiment Example 3).

Figure 14:
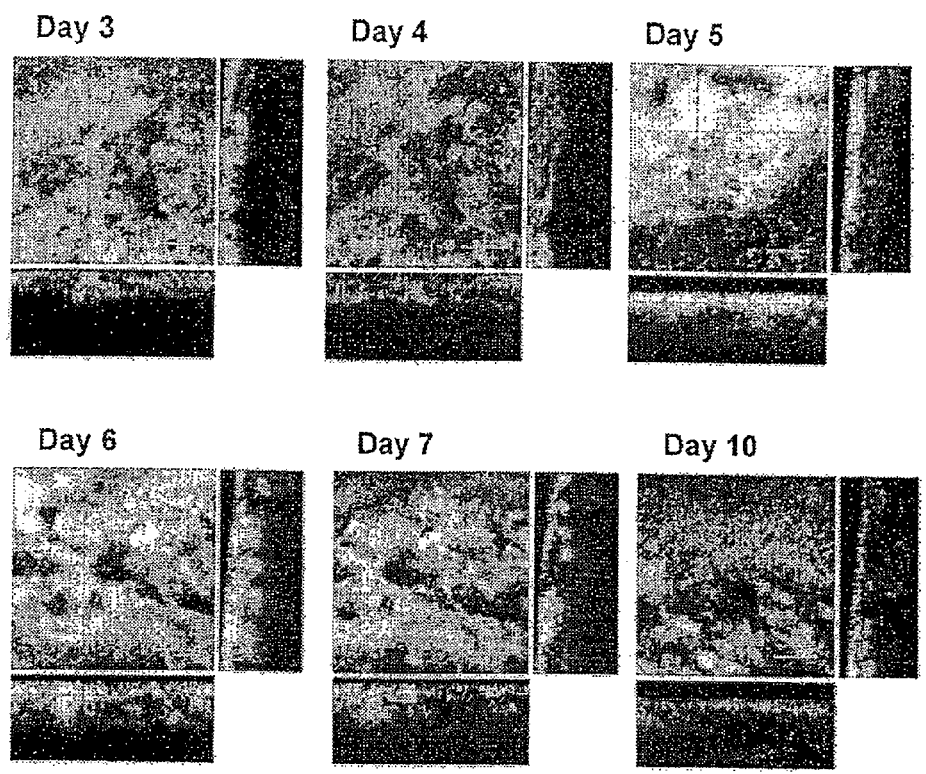

FIG. 14 shows the state of biofilm removal when using a test liquid (Comparative Compound 1, 100 μM) (Experiment Example 3).

Figure 15:
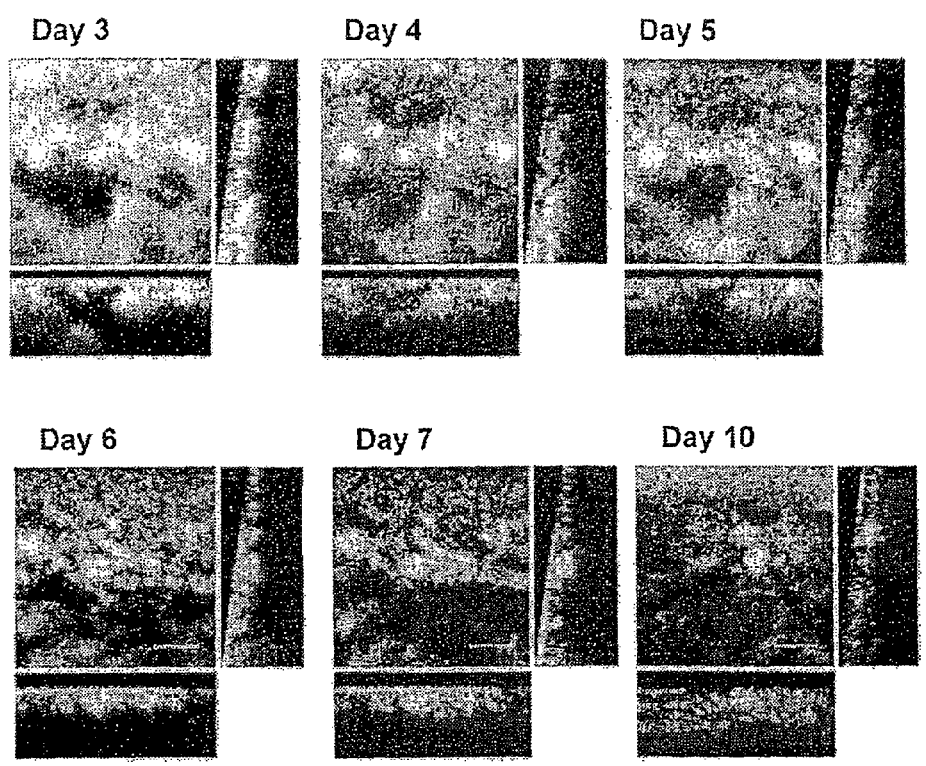

FIG. 15 shows the state of biofilm removal when using a test liquid (Comparative Compound 2, 100 μM) (Experiment Example 3).

Figure 16:
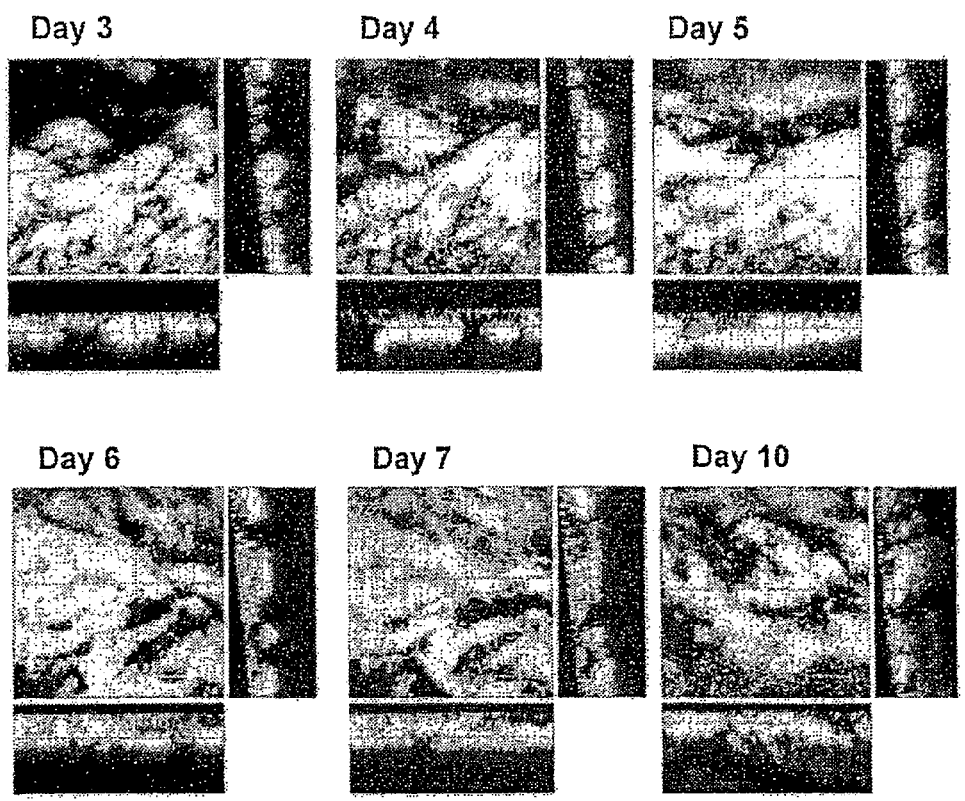

FIG. 16 shows the state of biofilm removal when using a test liquid (Comparative Compound 3, 100 μM) (Experiment Example 3).

BEST MODE FOR CARRYING OUT THE INVENTION (I) A New Amide Compound or Salt Thereof The present invention provides a new amide compound serving to strip off or remove deposited biofilms, or to inhibit biofilm formation. The amide compound or salt thereof is useful for an active ingredient of the later-described biofilm remover or biofilm formation inhibitor. The present invention also provides a new amide compound and salt thereof having disinfecting activity. The amide compound or salt thereof is useful for an active ingredient of the later-described disinfectant.

The "biofilm" of the present invention refers to a mucous film-like secretion, formed by microorganisms, that adheres to the surfaces of solids. In the biofilm, plural kinds of coexisting microorganisms form a complex (colony). The "biofilm" may also be described as an aggregation of microorganisms, surrounded by slime-like excrement generated by the microorganisms. The biofilm can adhere to inert solids, or solids such as polymers, plastics, ceramics, metals, glass, or hydroxyapatites that lack a self-governing ability. Additionally, the solid can, of course, be skin, bones, teeth, gingiva, tissues or any other parts of living organisms.

The amide compound is expressed by the following General Formula (1).

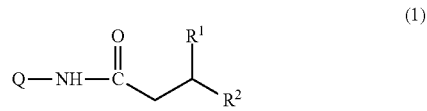

(1)

wherein $R^1$ is a hydrogen atom or a hydroxyl group, $R^2$ is a $C_{5-12}$ alkyl group, and Q is a substituent denoted by Formula (Q1) or (Q2),

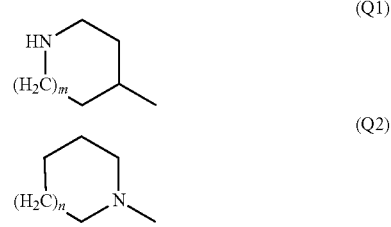

wherein n and m are 0 or 1.

In Formula (1), $R^2$ denotes a $C_{5-12}$ alkyl group including a straight chain or branched-chain $C_{5-12}$ alkyl group, such as n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, n-hexyl, 1-methyl-n-pentyl, 2-methyl-n-Pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, 1-methyl-1-ethyl-n-pentyl, n-heptyl, 2-heptyl, 1-ethyl-1,2-dimethyl-n-propyl, 1-ethyl-2,2-dimethyl-n-propyl, n-octyl, 3-octyl, 4-methyl-3-n-heptyl, 6-methyl-2-n-heptyl, 2-propyl-1-n-heptyl, 2,4,4-trimethyl-1-n-pentyl, n-nonyl, 2-nonyl, 2,6-dimethyl-4-n-heptyl, 3-ethyl-2,2-dimethyl-3-n-pentyl, 3,5,5-trimethyl-1-n-hexyl, n-decyl, 2-decyl, 4-decyl, 3,7-dimethyl-1-n-octyl, 3,7-dimethyl-3-n-octyl, n-undecyl, or n-dodecyl.

The straight chain or branched-chain $C_{5-12}$ alkyl group is more preferably the straight chain or branched-chain $C_{7-11}$ alkyl group, further preferably $C_{7-10}$ alkyl group. Examples of the particularly-preferable alkyl group include straight-chain n-heptyl group, n-octyl group, n-nonyl group, n-decyl group, and n-undecylic group.

In General Formula (1), $R^2$ may be a hydrogen atom or a hydroxyl group; however, a hydrogen atom is preferred.

In General Formula (1), the substituent expressed as Q may be a substituent expressed as Q1 in which m=0 (3-pyrrolidinyl group) or in which m=1 (4-piperidyl group). The substituent expressed as Q may be a substituent expressed as Q2 in which n=0 (1-pyrrolidinyl group) or in which n=1 (1-piperidyl group).

More specifically, the amide compound of the present invention denoted by Formula (1) can be specifically expressed as an amide compound denoted by the following formulas (1a) to (1d).

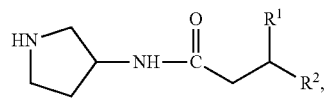

(1a)

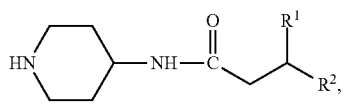

(1b)

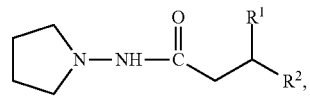

(1c)

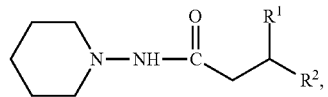

(1d)

wherein $R^1$ and $R^2$ are the same as those above.

More specifically, the compound denoted by Formula (1a) corresponds to a compound denoted by General Formula (1) in which the substituent Q is Q1 wherein m=0. The compound denoted by Formula (1b) corresponds to a compound denoted by General Formula (1) in which the substituent Q is Q1 wherein m=1. Similarly, the compound denoted by Formula (1c) corresponds to a compound denoted by General Formula (1) in which the substituent Q is Q2 wherein n=0. The compound denoted by Formula (1d) corresponds to a compound denoted by General Formula (1) in which the substituent Q is Q2 wherein n=1.

The amide compound according to the present invention is preferably an amide compound denoted by the Formulas (1a) to (1d) wherein $R^1$ is hydrogen atom, $R^2$ is straight-chain $C_{5-12}$ alkyl group, more preferably $C_{7-11}$ alkyl group, further preferably $C_{7-10}$ alkyl group. In this compound, $R^2$ is preferably a straight-chain alkyl group such as n-heptyl group, n-octyl group, n-nonyl group, or n-decyl group.

Note that, the amide compound denoted by Formula (1a) includes an isomer denoted by the following formula (1a') or (1a''). More specifically, the isomers 1a' and 1a'' may be used solely or in combination, as an active ingredient of a biofilm remover, biofilm formation inhibitor or disinfectant.

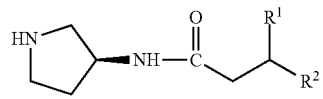

(1a')

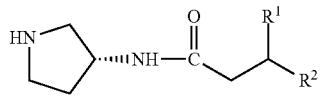

(1a'')

wherein $R^1$ and $R^2$ are the same as those above.

The amide compound denoted by Formula (1) of the present invention forms salt with an acid. The acid that forms salt with the amide compound (1) is not particularly limited, but an acid for pharmaceutical use is preferred. Examples of the acid include inorganic acids such as hydrochloric acid, nitric acid, sulfuric acid, or phosphoric acid; and organic acids such as formic acid, acetic acid, tartaric acid, maleic acid, malic acid, citric acid, salicylic acid, benzoic acid or ascorbic acid.

The amide compound (1) used for the present invention can be manufactured by a method denoted by Reaction Formula 1, for example.

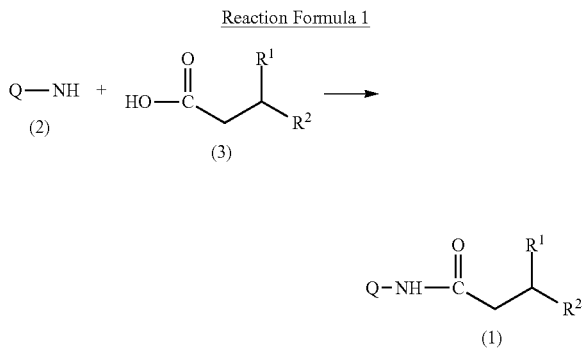

Reaction Formula 1 wherein Q, $R^1$ and $R^2$ are the same as those above.

According to Reaction Formula 1, the amide compound (1) of the present invention can be produced by reacting the amine compound denoted by Formula (2) and the carboxylic acid compound denoted by Formula (3).

This reaction is carried out in an inactive solvent in the presence of an appropriate condensing agent. Examples of the condensing agent include an acid halide forming agent such as phosphorus trichloride, phosphorus tribromide, phosphorus pentachloride, phosphorus oxychloride, thionyl chloride; a mixed acid anhydride forming agent such as ethyl chloroformate, or chlorinated methane sulfonyl; carbodiimides such as N,N'-dicyclohexyl carbodiimide (DCC), diisopropyl carbodiimide, or 1-ethyl-3-dimethylaminopropyl carbodiimide. Other condensing agents such as N,N-carbonyldiimidazole, 2-ethoxy-N-ethoxycarbonyl-1,2-dihydroquinoline (EEDQ), or triphenylphosphine-carbon tetrachloride (complex) may also be used.

The inactive solvent is not particularly limited. Examples of the inactive solvent includes aromatic hydrocarbons such as benzene, toluene, or xylene; halogenated aromatic hydrocarbons such as chlorobenzene, or dichloro benzene; aliphatic hydrocarbons such as hexane, cyclohexane, or petroleum ether; halogenated aliphatic hydrocarbons such as dichloromethane, 1,2-chloroethane, chloroform, or carbon tetrachloride; ethers such as diethylether, diisopropylether, dioxane, tetrahydrofuran, ethyleneglycoldimethylether, or ethyleneglycoldiethylether; ketones such as acetone, 2-butanone, or methylisobutylketone; nitriles such as acetonitrile, propionitrile, or benzonitrile; amides such as N,N-dimethylformamide, or hexamethylphosphoric triamide (RMPA); sulfoxides such as dimethylsulfoxide; and mixtures of those.

According to Reaction Formula 2, the amide compound (1) of the present invention can also be produced by reacting the amine compound denoted by Formula (2) and the carboxylic acid halogenide denoted by Formula (4) in an appropriate solvent, and if necessary, in the presence of a base.

Reaction Formula 2

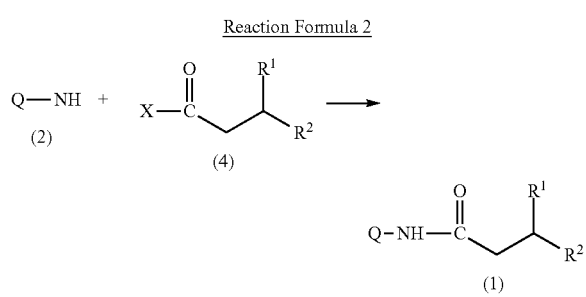

wherein Q, $R^1$ and $R^2$ are the same as those above, and X denotes halogen atom.

An inactive solvent similar to that used in the reaction denoted by Reaction Formula 1 may be used in this reaction.

As mentioned above, the reaction may be carried out in the presence of a base as necessary. Examples of the base include alkali metal or alkaline-earth metal hydroxides such as sodium hydroxide, potassium hydroxide or calcium hydroxide; alkali metal carbonate or hydrogen carbonates such as sodium carbonate, potassium carbonate, sodium hydrogencarbonate, or potassium hydrogencarbonate; alkali metal or alkaline-earth metal acetates such as sodium acetate, potassium acetate, or calcium acetate; alkali metal or alkaline-earth metal hydrides such as sodium hydride, potassium hydride or calcium hydride; ammonium salts such as ammonium hydroxide, ammonium bicarbonate or ammonium acetate; and tertiary amines such as trimethyl amine, triethyl amine, N,N-dimethylaniline, pyridine, 4-(dimethylamino) pyridine, diaza-bicyclo-octane (DABCO), diaza-bicyclononene (DBN), or diaza-bicycloundecen (DBU).

The amounts of reagents used in the reaction are not particularly limited, but the amount of the amine compound (2) preferably ranges from 0.8 to 5 mol, more preferably 1 to 3 mol, per mol of the carboxylic acid compound (3) or the carboxylic acid halogenide (4). In the reaction denoted by Reaction Formula 1, the amount of the condensing agent typically ranges from 0.8 to 5 mol, more preferably 1 to 3 mol, per mol of the carboxylic acid compound (3). When using a base in the reaction denoted by Reaction Formula 2, the amount of the base typically ranges from 0.8 to 5 mol, more preferably 1 to 3 mol, per mol of the carboxylic acid halogenide (4).

The reaction temperature is not particularly limited, but typically set in a range from −10° C. up to the boiling point of the solvent. The reaction time varies depending on the above-mentioned amount or temperature, but is typically controlled between 5 to 10 hours.

Note that, the amine compound (2), carboxylic acid compound (3) and carboxylic acid halogenide (4) used in the foregoing reactions are all commercially available or can be manufactured easily by a known method.

The target amide compound (1) thus obtained can be easily refined by being isolated from the reaction mixture via general isolation such as column chromatography or recrystallization.

(II) Biofilm Remover (Biofilm Stripping Agent), Biofilm Formation Inhibitor, Disinfectant As shown in the later-described experiment example, the amide compound (1) and salt thereof according to the present invention is capable of stripping off or removing biofilms, inhibiting formation of biofilms, and disinfecting activity.

With these properties, the amide compound (1) and salt thereof according to the present invention is useful for an active ingredient of a composition for stripping off or removing biofilms, or preventing formation of biofilms (biofilm remover or biofilm formation inhibitor), or an active ingredient of a composition for a bactericidal composition (bactericide).

The amide compound (1) and salt thereof according to the present invention serves as an effective biofilm remover or biofilm formation inhibitor, and is effective against various bacterias forming biofilms and biofilms formed by the bacteria. The range of bacteria is limitless, and includes Pseudomonas aeruginosa (Pseudomonas aeruginosa), periodontitis pathogenic bacteria, E. Coli, and staphylococcus aureus. The amide compound (1) and salt thereof of the present invention is particularly effective against Pseudomonas aeruginosa (Pseudomonas aeruginosa), periodontitis pathogenic bacteria, and biofilms formed by these bacterias.

The amide compound (1) and salt thereof according to the present invention serves as a disinfectant particularly effective against Pseudomonas aeruginosa (Pseudomonas aeruginosa), E. Coli, and staphylococcus aureus.

The present invention thus provides a biofilm remover, biofilm formation inhibitor, or disinfectant containing the amide compound (1) or the salt thereof as an active ingredient (the biofilm remover, biofilm formation inhibitor or disinfectant may be hereinafter referred to as "formulation").

The formulation of the present invention may be the amide compound (1) or the salt thereof itself, or a composition made by mixing an arbitrary carrier or additive with the amide compound (1) or a salt thereof and processing the mixture into a desired form with a known method according to the usage. Though it is not particularly limited, the form of the present invention includes solid products such as tablets, powders, granules, pills, powder syrups or capsules (hard capsules, soft capsules); paste or gel products such as creams, ointments or gels; and liquid products such as solutions, suspensions or emulsions, syrups, elixirs, sprays or aerosols.

Insofar as the resulting formulation ensures sufficient biofilm removal effect, inhibitory effects against biofilm formation, or disinfecting activity, the content of the amide compound (1) or salt thereof in the formation of the present invention is not limited. In other words, to ensure the desired biofilm removal effect, the content of the amide compound (1) or salt thereof should be adjusted in a range from 0.001 to 99 wt %, preferably 0.01 to 50 wt % or 0.05 to 10 wt %, per 100 wt % of the formulation.

The formulation of the present invention thus contains the amide compound (1) or salt thereof at a ratio to ensure the biofilm removal effect, inhibitory effects against biofilm formation, or disinfecting activity, and may contain other components according to the usage or purpose of the formulation insofar as the biofilm removal effect, inhibitory effect against biofilm formation, or disinfecting activity is not impaired. Though it is not particularly limited, possible examples of the other components include general carriers for drug formulation such as diluent bases, binders, dispersants, viscosity improvers, lubricants, pH adjusters, solubilizing agents; and other agents such as antibiotics, antimicrobial agents, disinfectants, antiseptics, builders, bleaches, enzymes, chelating agents, antifoaming agents, colorants (dyes, pigments, etc.), softening agents, moisturizers, surfactants, antioxidants, perfumes, corrective substances, odor-masking agents and solvents.

In addition to the amide compound (1) or salt thereof, the formulation of the present invention may contain an antimicrobial agent or a disinfectant, for example, a tetracycline disinfectant such as minocycline hydrochloride; cation disinfectants such as triclosan, cetylpyridinium chloride, or benzethonium chloride; or macrolide antibiotic.

The formulation of the present invention may also contain compounds for improving the disinfecting effect or the activity of the antimicrobial agent or disinfectant. Examples of the compound include basic amino acids such as arginine, lysine, or histidine; various enzymes including starch modification enzymes such as farnesol, transglucosidase, or CGTase; and starch hydrolases such as α-amylase.

The formulation of the present invention is applicable anywhere a biofilm has developed to detrimental effect, or anywhere requiring disinfection.

The formulation of the present invention can be used, for example, in the following manner to remove biofilms deposited in industrial areas, circulating-type bathtubs, or the like. The formulation of the present invention, having been processed into a suspension liquid, water-dispersible powder, or water-soluble powder, is circulated in the pipes of the target equipment, or sprayed on the target portion of the equipment. The formulation of the present invention can also take the form of a high-concentration liquid, or a solid preparation such as tablet, powder, or a grain agent supplied to a water tank so that the remover diluted or dissolved in the water is applied to the target portion. Further, the formulation of the present invention can be processed into medicinal preparations suitable for oral administration, parenteral administration, or local administration. Moreover, as described later, the formulation of the present invention can be processed into various oral-sanitation products such as toothbrushing agents, mouth deodorants, mouth washes, gingival medicines, gums, gargles, artificial teeth, or cleaning agents for dental materials.

The appropriate usage quantity of the formulation of the present invention varies depending on the target object or dosage form (it differs particularly for sustained-release formulation), and therefore cannot be clearly defined. However, when used to prevent or treat biofilm infection, for example, an appropriate per-day dosage amount of the formulation of the present invention is typically 1 ng/mL to 100 mg/mL, preferably 10 ng/mL to 10 mg/mL, in the absolute quantity, typically ing to 500 mg, on the basis of the dosage of the amide compound (1) or salt thereof of the present invention (e.g., the gross quantity for humans is 300 mg).

(III) Oral Composition

The present invention provides an oral composition containing the biofilm remover, the biofilm formation inhibitor, or the disinfectant. The present invention was made based on the fact that the biofilm remover or the biofilm formation inhibitor of the present invention containing the amide compound (1) or salt thereof as an active ingredient has a particularly notable effect of removing/inhibiting a biofilm formed by periodontitis pathogenic bacteria, and that the disinfectant of the present invention containing the amide compound (1) or salt thereof as an active ingredient has particularly notable disinfecting activity with respect to bacterias.

Examples of periodontitis pathogenic bacterias forming biofilms include *Porphyromonas gingivalis, Tannerella forsythensis, Actinobacillus actinomycetemcomitans, Prevotella intermedia, Eikenella corrodens, Campylobacter rectus, Fusobacterium necleatum*, and *Treponema denticola*.

The oral composition according to the present invention is typically a composition dedicatedly used for oral treatments to prevent or treat oral diseases such as periodontitis related to pathogenic bacteria. Examples of such compositions include toothbrushing agents such as tooth pastes, toothbrushing powders, toothbrushing liquids, or infiltrative toothbrushing agents; mouth deodorants and mouth washes in the form of troches, tablets, liquids, gums, oleasters or films; and gingival medicines in the form of creams, ointments, or gels. The oral composition according to the present invention may also be a composition used dedicatedly for the care of medical oral materials, such as artificial teeth or other dental materials, to prevent oral diseases. Examples of such compositions include cleaning agents for artificial teeth or dental materials.

The proportion of the biofilm remover, the biofilm formation inhibitor, or the disinfectant in the oral composition is preferably adjusted so that the content (gross amount) of the amide compound (1) or salt thereof, that is an active ingredient of the remover, inhibitor or disinfectant, falls within a range from 0.001 to 99 wt %, preferably 0.01 to 50 wt %, more preferably 0.05 to 10 wt %, per 100 wt % of the composition.

According to the type or form of the composition, as needed, the oral composition of the present invention may contain the following components in a general usage range, in addition to the foregoing components.

Abrasive

Silica abrasives such as silica gel, precipitable silica, igneous silica, hydrous silicic acid, anhydrous silicic acid, titanium silicate, zeolite, aluminosilicate and zirconosilicate; and monobasic calcium phosphate, dibasic calcium phosphate dihydrate, dibasic calcium phosphate non-hydrates, calcium pyrophosphate, tribasic magnesium phosphate, tribasic calcium phosphate, aluminum hydroxide, alumina, calcium carbonate light, calcium carbonate heavy, magnesium carbonate, tribasic magnesium phosphate, zirconium silicate, insoluble sodium metaphosphate, insoluble calcium metaphosphate, titanium oxide, and synthetic resin abrasive. These abrasives may be used solely or in combination. When incorporating such abrasives (e.g., in dentifrices), the amount is not particularly limited, but preferably 3 to 80 wt %, and more preferably 10 to 50 wt %, per 100 wt % of oral composition.

Humectant and Viscous Agent

Polyhydric alcohols such as glycerin, concentrated glycerin, diglycerin, ethylene glycol, dipropylene glycol, polyethylene glycol, propylene glycol, polypropylene glycol, or 1,3-butyleneglycol; and sugar-alcohols such as xylitol, maltitol, or lactol. These humectants and viscous agents may be used solely or in combination.

Binder

Alginates and derivatives thereof such as alginic acid, sodium alginate, propylene glycol alginate ester, calcium-containing sodium alginate, potassium alginate, calcium alginate, ammonium alginate; gums such as carrageenan (mainly Iota; Lambda; and Kappa), xanthan gum, tragacanth, karaya gum, gum arabic, locust bean gum, or guar gum; celluloses such as carboxymethylcellulose sodium, methylcellulose, ethylcellulose, cellulose acetate, or hydroxyethylcellulose sodium; gelatin, agar, polyvinyl alcohol, sodium polyacrylate, carboxyvinyl polymer, polyvinyl pyrrolidone, carbopol, silica gel, aluminium silica gel, and thickening nature silica. These binders may be used solely or in combination. When incorporating such binders (e.g., in dentifrices), the amount is not particularly limited, but preferably 0.1 to 10 wt %, per 100 wt % of oral composition.

Foaming Agent

Sodium lauryl sulfate, lauroylsarcosine sodium, alkyl sulfo monosodium succinate, palm-oil-fatty-acid mono-glycerol sulfone sodium, α-olefin sulfone sodium, N-acylamino acid salt such as N-acylglutamate, 2-alkyl-N-carboxymethyl-N-hydroxyethyl imidazolinium betaine, maltitol fatty acid ester, sucrose fatty acid ester, polyglyceryl fatty acid ester, fatty acid diethanolamide, polyoxyethylenesorbitan monostearate, polyoxyethylene hydrogenated castor oil, or polyoxyethylene fatty acid ester. These foaming agents may be used solely or in combination.

Surfactant

As the surfactant, anion surfactants, cation surfactants, nonionic surfactants, and amphoteric surfactants are all applicable.

Examples of anion surfactants include sodium lauryl sulfate, sodium myristyl sulfate, N-lauroylsarcosinic acid sodium salt, N-myristoylsarcosinic acid sodium salt, sodium dodecylbenzenesulfonate, hydrogenation coconut fatty acid monoglyceride mono-sodium sulfate, sodium lauryl sulfosulfate, α-olefin sulfonate sodium, N-acylglutamates such as N-palmitoyl sodium glutamate, and N-acyltaurates such as N-methyl-N-acyltaurine sodium. Examples of nonionic surfactants include sucrose fatty acid esters such as sucrose fatty acid ester or maltose fatty acid ester, sugar-alcohol fatty acid esters such as maltitol fatty acid ester and lactol fatty acid ester, alkylol amide, polyoxyethylene sorbitan fatty acid esters such as polyoxyethylenesorbitan monostearate, polyoxyethylene fatty acid esters such as polyoxyethylene hydrogenated castor oil, fatty acid ethanolamides such as lauryl acid mono- or di-ethanolamide, sorbitan fatty acid ester, polyoxyethylene higher alcohol ether, polyoxyethylene polyoxypropylene copolymer, polyoxyethylene polyoxypropylene fatty acid ester, polyglyceryl fatty acid ester, and Pluronic. Examples of amphoteric surfactants include 2-alkyl-N-carboxymethyl-N-hydroxyethyl imidazolium betaine, N-alkyldiaminoethyl glycine such as N-lauryl diaminoethyl glycine or N-myristyl diaminoethyl glycine, and N-alkyl-1-hydroxyethylimidazolin betaine sodium. These surfactants may be used solely or in combination.

Sweetening Agent

Saccharin sodium, aspartame, stevioside, *stevia* extract, paramethoxy cinnamic aldehyde, neohesperidyl dihydrochalcone, perillartine, glycyrrhizine, and thaumatin. These sweetening agents may be used solely or in combination.

Antiseptic

Parabens such as methylparaben, ethylparaben, propylparaben, or butylparaben; sodium benzoate, phenoxyethanol, and alkyldiaminoethylglycine hydrochloride. These antiseptics may be used solely or in combination.

Aromatic Component 1-menthol, anethole, menthone, cineole, limonene, carvone, methyl salicylate, ethyl butyrate, eugenol, thymol, n-decylalcohol, citronellol, α-terpineol, citronellyl acetate, linalool, ethyl linalool, vanillin, peppermint, cinnamic aldehyde, and trans-2-hexenal. These aromatic components may be used solely or in combination. Note that, these components may be purified products, or may be crude products of essential oils containing these components (for example, lemon oil, orange oil, sage oil, rosemary oil, *cassia* and cinnamon oil, pimento oil, cinnamon leaf oil, beefsteak plant oil, wintergreen oil, oil of cloves, or *eucalyptus* oil).

Further, in addition to the foregoing aromatic components, other components or essential oils such as aliphatic alcohol or esters thereof, terpene carbon hydride, phenolether, aldehyde, ketone, or lactone may be used insofar as the effects of the present invention are not impaired. The amount of these aromatic components is preferably 0.02 to 2 wt %, per 100 wt % of the whole oral composition.

Antimicrobial Component

Antibacterial metals such as silver, copper, zinc, or metal salts thereof with low water solubility (e.g., silver oxide, silver chloride, silver carbonate, silver phosphate, copper hydroxide, copper gluconate, zinc oxide, zinc citrate, zinc stearate, and zinc trichlorophenate, zinc hydroxide, zinc oxalate, zinc phosphate), copper chlorophyll, cetylpyridium chloride, benzalkonium chloride, triclosan, hinoki thiol, lysozyme chloride.

Antiseptic Component

Nonionic antimicrobial agents such as parabens, sodium benzoate or triclosan; cationic antiseptic agents such as benzethonium chloride or cetylpyridinium chloride.

Oral Active Ingredient

Lysozyme chloride, sodium fluoride, potassium fluoride, sodium monofluorophosphate, polyethyleneglycol, polyvinyl pyrrolidone, hinoki thiol, ascorbic acid, ascorbic acid salts, chlorhexidine salts, cetylpyridinium chloride, benzalkonium chloride, benzethonium chloride, bisabolol, triclosan, isopropylmethylphenol, tocopherol acetate, epsilon (ε)-aminocaproic acid, tranexamic acid, aluminium hydroxyl allantoin, aluminum lactate, dihydrocholesterol, glycyrrhetinic acid, glycyrrhizinates, copper chlorophyllin salt, sodium chloride, guaiazulene sulfonate, dextranase, pyridoxine hydrochloride, tranexamic acid, sodium chloride, Vitamins C and E, various enzymes (e.g., dextranase, amylase, protease, mutanase, or pectinase), tartar control agents such as azulene or polyphosphate, nicotine removers such as polyethylene glycol or polyvinyl pyrrolidone, and hyperesthesia prophylactic agents such as aluminum lactate or potassium nitrate. These oral active ingredients may be used solely or in combination.

Other Additives

Pigments such as Food Blue No. 1, titanium oxide, antioxidants such as dibutylhydroxytoluene, and flavoring substances such as tea leaf dry distilled solution or sodium glutamate.

The oral composition of the present invention can be manufactured by any common procedure. The production of the oral composition in the form of, for example, toothpaste, is completed by being packed in an aluminium tube, laminated tube, glass evaporation tube, plastic tube, plastic bottle, aerosol container or the like before being marketed to allow the consumer to apply it to the target portion.

The oral composition of the present invention prevents formation of biofilms by periodontitis pathogenic bacteria in the mouth and removes the formed intraoral biofilms, thereby effectively preventing generation of bacterial flora. Further, by incorporating an antimicrobial agent in the remover, the improved antimicrobial effect will further increase the quality of the oral composition. Therefore, the oral composition of the present invention is effective for the prevention or treatment of periodontosis and periodontal diseases (for example, gingivitis). Further, the oral composition of the present invention is effective for the prevention or removal of oral odor due to periodontosis or periodontal diseases (for example, gingivitis).

EXAMPLES

The following describes production examples and experiment examples of the amide compound (1) according to the present invention to more specifically explain the present invention. However, the present invention is not limited to these examples.

Production Example 1

Production of N-(pyrrolidin-3-yl) dodecanoyl amide (1a-1)

0.22 g (1 mmol) of dodecanoyl chloride and 0.18 g (2.1 mmol) of 3-aminopyrrolidine are dissolved in 10 ml of dichloromethane. The solution was stirred while cooled with ice for 12 hours. The reaction liquid was concentrated under reduced pressure. The resultant residue was subjected to extraction with ethyl acetate. The obtained ethyl acetate layer was washed with diluted hydrochloric acid and saturated saline, dried with magnesium sulfate, and concentrated under reduced pressure. The resulting residue was purified by silica gel chromatography (developing solvent: hexane/ethyl acetate=3/7) to obtain a N-(pyrrolidin-3-yl) dodecanoyl amide (Compound 1a-1) denoted by the following formula.

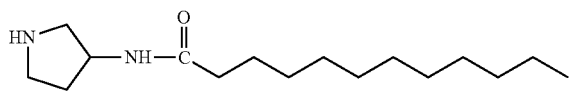

(1a-1)

Quantity Yield: 0.18 g (0.69 mmol)

Percent Yield: 69%

$^1$H-NMR(CDCl$_3$, 500 MHz):0.90 ppm (t, 3H), 1.28 ppm (m, 16H), 1.64 ppm (t, 2H), 1.76 ppm (m, 1H), 2.00 ppm (br, 1H), 2.13 ppm (m, 1H), 2.27 ppm (t, 2H), 3.24 ppm (m, 1H), 3.51 ppm (m, 1H), 3.67 ppm (m, 3H).

Production Example 2

Production of N-(pyrrolidin-3-yl) decanoyl amide (Compound 1a-2)

The same process as that of Production Example 1 was conducted except that decanoyl chloride was used in place of dodecanoyl chloride to obtain N-(pyrrolidin-3-yl) decanoyl amide (Compound 1a-2) denoted by the following formula.

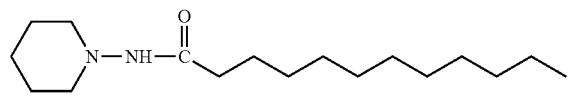

(1d-1)

Quantity Yield: 0.15 g (0.62 mmol)

Percent Yield: 62%

$^1$H-NMR (CDCl$_3$, 500 MHz):0.88 ppm (t, 3H), 1.29 ppm (m, 12H), 1.65 ppm (m, 2H), 1.88 ppm (m, 1H), 2.10 ppm (m, 1H), 2.26 ppm (m, 2H), 3.21 ppm (m, 1H), 3.49 ppm (m, 1H), 3.65 ppm (m, 3H), 8.59 ppm (br, 1H).

Production Example 3

Production of N-(piperidine-4-yl) dodecanoyl amide (1b-1)

The same process as that of Production Example 1 was conducted except that 4-aminopiperidine was used in place of 3-aminopyrrolidine to obtain N-(piperidine-4-yl) dodecanoyl amide (1b-1) denoted by the following formula.

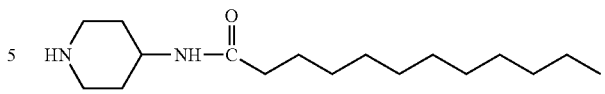

(1b-1)

Quantity Yield: 0.16 g (0.56 mmol)

Percent Yield: 56%

$^1$H-NMR (CDCl$_3$, 500 MHz):0.88 ppm (t, 3H), 1.27 ppm (m, 18H), 1.59 ppm (m, 2H), 1.86 ppm (m, 2H), 2.30 ppm (t, 2H), 2.68 ppm (t, 1H), 2.89 ppm (m, 1H), 3.05 ppm (t, 1H), 3.71 ppm (d, 1H), 4.51 ppm (d, 1H).

Production Example 4

Production of N-(piperidine-4-yl) decanoyl amide (1b-2)

The same process as that of Production Example 1 was conducted except that 4-aminopiperidine was used in place of 3-aminopyrrolidine, and decanoyl chloride was used in place of dodecanoyl chloride to obtain N-(piperidine-4-yl) decanoyl amide (1b-2) denoted by the following formula.

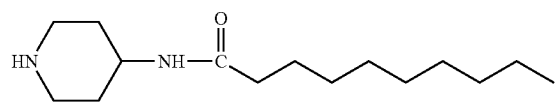

(1b-2)

Quantity Yield: 0.16 g (0.64 mmol)

Percent Yield: 64%

$^1$H-NMR (CDCl$_3$, 500 MHz):0.87 ppm (t, 3H), 1.25 ppm (m, 14H), 1.59 ppm (m, 2H), 1.82 ppm (m, 2H), 2.31 ppm (m, 2H), 2.67 ppm (t, 1H), 2.90 ppm (m, 1H), 3.06 ppm (m, 1H), 3.81 ppm (m, 1H), 4.50 ppm (m, 1H), 8.00 ppm (br, 1H).

Production Example 5

Production of N-(pyrrolidin-1-yl) dodecanoyl amide (Compound 1c-1)

The same process as that of Production Example 1 was conducted except that 1-aminopyrrolidine was used in place of 3-aminopyrrolidine to obtain N-(pyrrolidin-1-yl) dodecanoyl amide (Compound 1c-1) denoted by the following formula.

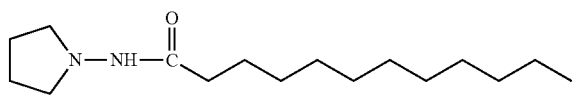

(1c-1)

Quantity Yield: 0.21 g (0.78 mmol)

Percent Yield: 78%

$^1$H-NMR (CDCl$_3$, 500 MHz):0.88 ppm (t, 3H), 1.28 ppm (m, 16H), 1.62 ppm (m, 2H), 1.88 ppm (m, 5H), 2.06 ppm (m, 1H), 2.47 ppm (m, 2H), 2.91 ppm (t, 2H), 6.11 ppm (br, 1H).

Production Example 6

Production Example 6 of N-(pyrrolidin-1-yl)-3-hydroxy dodecanoyl amide (Compound 1c-2)

(1) Synthesis of 3-hydroxydecanoic acid ethyl ester 7.8 g of zinc activated by a hydrochloric acid and 25 ml of benzene were placed in a circulation device incorporating the Dean and Stark device. The solution was circulated while heated. To the resultant solution, a mixed solution of 15.6 g (100 mmol) of decanal and 18.4 g (110 mmol) of bromoacetic acid ethyl was dropped. After six hours, the solution was cooled to room temperature. A 50%(w/w) sulfuric acid was added to divide the solvent, and the organic layer was separated. The organic layer was dried with magnesium sulfate, and concentrated under reduced pressure. The resulting residue was purified by silica gel chromatography (developing solvent: hexane/ethyl acetate=2/8). As a result, a 3-hydroxydecanoic acid ethyl ester was obtained.

Quantity Yield: 30.6 g (93 mmol)
Percent Yield: 93%
$^1$H-NMR (CDCl$_3$, 500 MHz):0.91 ppm (t, 3H), 1.28 ppm (m, 17H), 1.44 ppm (m, 2H), 2.43 ppm (m, 2H), 4.02 ppm (m, 1H), 4.18 ppm (q, 2H).

(2) Production of 3-hydroxydecanoic acid 16.5 g (50 mmol) of the 3-hydroxydecanoic acid ethyl ester obtained in the process (1) and 10.0 g (250 mmol) of lithium hydroxide were dissolved in a mixed solution of 50 mL of tetrahydrofuran and 100 mL of water, and the solution was stirred at room temperature for 12 hours. The reaction liquid was neutralized by diluted hydrochloric acid, and was concentrated under reduced pressure. The residue was subjected to extraction with ethyl acetate. The obtained ethyl acetate layer was washed with saturated saline, dried with magnesium sulfate, and concentrated under reduced pressure. The resulting residue was purified by silica gel chromatography (developing solvent: ethyl acetate/methanol=4/6) to obtain 3-hydroxydecanoic acid (Percent Yield=90%).

Quantity Yield: 12.2 g (45 mmol)
Percent Yield: 90%
$^1$H-NMR (CDCl$_3$, 500 MHz):0.86 ppm (t, 3H), 1.25 ppm (m, 14H), 1.33 ppm (m, 2H), 2.31 ppm (m, 2H), 3.79 ppm (m, 1H).

(3) Production of N-(pyrrolidin-1-yl)-3-hydroxy dodecanoyl amide 0.24 g (1.1 mmol) of 3-hydroxydodecanoic acid obtained in the process (2) and 0.09 g (1 mmol) of 1-aminopyrrolidine were dissolved to 10 ml of dichloromethane. 0.13 g (1.1 mmol) of dimethyl amino pyridine and 0.15 g (1.2 mmol) of diisopropylethylamine were added to the solution. Further, 0.21 g (1.1 mmol) of 1-ethyl-3-dimethylaminopropyl carbodiimide was added. The mixture was stirred at room temperature for 12 hours, and was concentrated under reduced pressure. The resultant residue was subjected to extraction with ethyl acetate. The obtained ethyl acetate layer was washed with saturated saline, dried with magnesium sulfate, and concentrated under reduced pressure. The resulting residue was purified by silica gel chromatography (developing solvent: ethyl acetate/methanol=8/2) to obtain N-(pyrrolidin-1-yl)-3-hydroxy dodecanoyl amide (Compound 1c-2) denoted by the following formula.

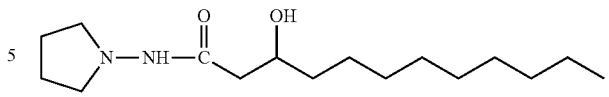

(1c-2)

Quantity Yield: 0.01 g (0.35 mmol)
Percent Yield: 35%
$^1$H-NMR (CDCl$_3$, 500 MHz):0.88 ppm (t, 3H), 1.26 ppm (m, 14H), 1.43 ppm (m, 2H), 1.58 ppm (m, 1H), 2.24 ppm (m, 3H), 2.55 ppm (m, 2H), 3.81 ppm (m, 2H), 3.86 ppm (m, 2H), 4.04 ppm (m, 1H).

Production Example 7

Production of N-(piperidine-1-yl) dodecanoyl amide (Compound 1d-1)

The same process as that of Production Example 1 was conducted except that 1-aminopiperidine was used in place of 3-aminopyrrolidine to obtain N-(piperidine-1-yl) decanoyl amide (1d-1) denoted by the following formula.

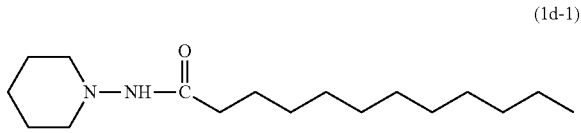

(1d-1)

Quantity Yield: 0.24 g (0.84 mmol)
Percent Yield: 84%
$^1$H-NMR (CDCl$_3$, 500 MHz):0.87 ppm (t, 3H), 1.31 ppm (m, 17H), 1.55 ppm (m, 7H), 2.06 ppm (dt, d=440 Hz, 2H), 2.48 ppm (dm, d=440 Hz, 2H), 2.67 ppm (dm, d=400 Hz, 2H), 6.32 ppm (br, 1H).

Experiment Example 1

Evaluation Test for Biofilm Formation Inhibition Effect Against *Pseudomonas aeruginosa*

Figure 1:
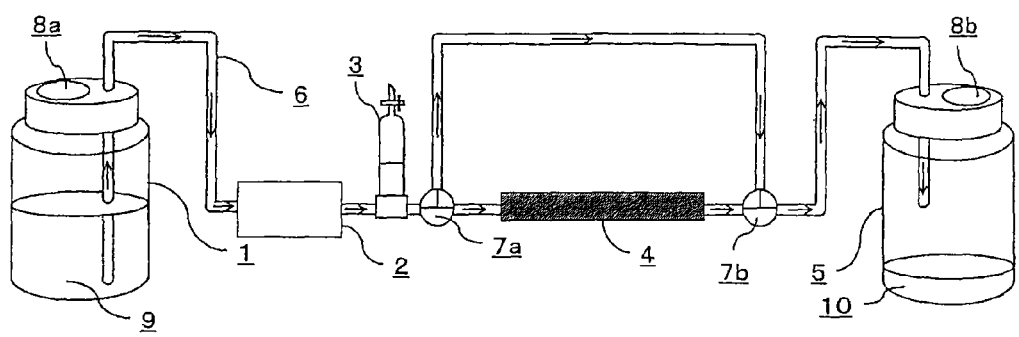
FIG. 1 shows a flow cell system. 1: Culture medium bottle (product of Nunc), 2: Pump (4-channel peristaltic pump ISM935: product of ISMATEC), 3: Air removal section (a modified stoppered glass column), 4: Glass cell (Observation Glass Capillary FC91 (1 mm×1 mm×14 mm): product of BioSurface Technology), 5: Waste fluid bottle (product of Nunc), 6: Silicon tube (φ1.5 mm), 7a, 7b: Three-way turncock (product of Termo), 8a, 8b: Membrane filter (0.44 μm: product of Millipore), 9: Culture medium, 10: Waste fluid.
Figure 2:
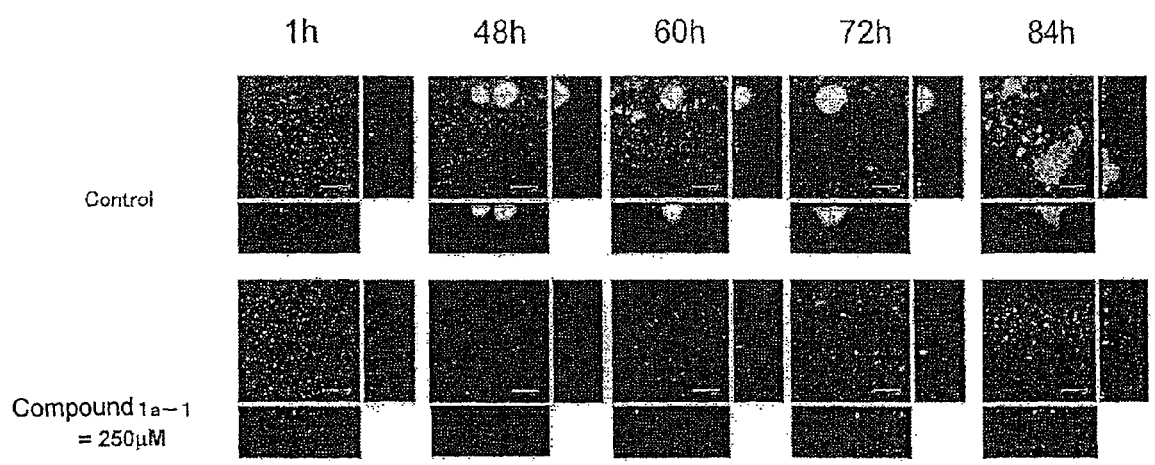
FIG. 2 shows a comparison between the state of biofilm formation when using a test liquid (Compound 1a-1, 250 μM)

With the flow cell system shown in FIG. 1, an inhibitory effect against biofilm formation by *Pseudomonas aeruginosa* was evaluated for each of the amide compounds produced in Production Examples 1, 3, 5, 6 and 7 (Compounds 1a-1, 1b-1, 1c-1, 1c-2, 1d-1), and for each of Comparative Compounds (Comparative Example) 1 to 3 denoted by the following formulas.

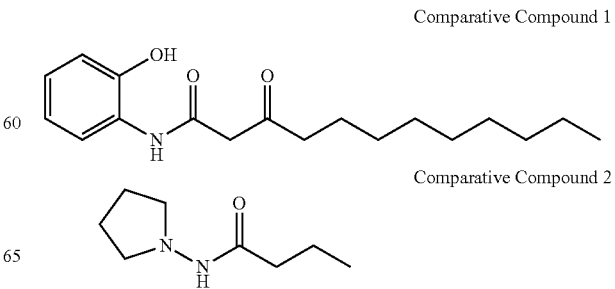

Comparative Compound 1

Comparative Compound 2

-continued

Comparative Compound 3

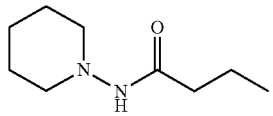

Flow Cell System (FIG. 1)

A culture medium bottle (1), a peristaltic pump (2), a glass cell (4) and a waste fluid bottle (5) are connected via a silicon tube (6) so that a culture medium (9) is supplied to the glass cell (4) from the culture medium bottle (1) using the peristaltic pump (2). The system includes an air removal section (3) between the peristaltic pump (2) and a turncock (7a), for removing the entrained air. All instruments in the flow cell system are sterilized using gamma-rays or an autoclave.

As specifically described later, the inhibitory effect against biofilm formation of each of the amide compounds is examined in the following manner. Bacteria are cultured in a glass cell (4) to grow a biofilm on the inner wall of the cell, and a test liquid containing one of the amide compounds is applied to the biofilm. Then the state of the biofilm is observed to evaluate the inhibitory effect against biofilm formation of the compound using a fluorescence confocal microscope (Leica TCS SP2: product of Leica).

Materials

Bacteria

The bacteria was prepared by inserting a pTdk-LVAgfp plasmid into a Pseudomonas aeruginosa PAO1-strain using the electroportion method so that the Pseudomonas aeruginosa PAO1-strain is transformed to express Green Fluorescent Protein (hereinafter referred to as "gfp expression PAO1-strain") (see Teresa R. et al., Applied and Environmental Microbiology, April 2001, p. 1865-1873).

Culture Medium

A 30 mM glucose-containing FAB culture medium was used for preincubation, and a 0.3 mM glucose-containing FAB culture medium was used for main cultivation.

Glucose-Containing FAB Culture Medium

The glucose-containing FAB culture medium was prepared by adding 200 μg/mL of carbenicillin to an aqueous solution containing 30 mM glucose or 0.3 mM glucose, 15 mM ammonium sulfate, 33.7 mM disodium hydrogenphosphate dihydrate, 22.1 mM potassium dihydrogen phosphate, 51.7 mM sodium chloride, 0.47 mM magnesium chloride, 0.08 mM calcium chloride and the following 0.1% trace metal solution.

Trace Metal Solution

An aqueous solution containing 1.16 mM calcium sulfate dihydrate, 0.72 mM iron sulfate heptahydrate, 0.08 mM manganous sulfate monohydrate, 0.08 mM copper sulfate pentahydrate, 0.07 mM zinc sulfate heptahydrate, 0.04 mM cobalt sulfate heptahydrate, 0.04 mM sodium permanganate monohydrate, and 0.08 mM boric acid.

Bacterial Suspension

A gfp expression PAO1-strain was inoculated in a 30 mM glucose-containing FAB culture medium, and was subjected to shake culture at 37° C. in an isothermal tank overnight. The obtained overnight culture liquid was diluted by a 30 mM glucose-containing FAB culture medium to $OD_{590}=0.1$.

Test Liquid and Control Test Liquid

Test Liquid

The test liquid was prepared by dissolving 100-250 μM of each of the Compounds 1a-1, 1b-1, 1c-1, 1c-2, or 1d-1 according to Production Examples 1, 3 and 5 to 7 and 100-250 μM of Comparative Compounds 1 to 3 as comparative examples in dimethyl sulfoxide (DMSO), and supplying the resulting DMSO solutions to a 0.3 mM glucose-containing FAB culture medium so that the concentration of each compound becomes 0.1%(v/v).

Control Test Liquid

A DMSO not containing the compound was used as a control test liquid.

Test Method

The flow cell system was filled with hydrous ethanol of 70 volume %, and was allowed to stand for at least 12 hours to sterilize the system. Then, air having been filtrated by a membrane filter (8a) was supplied into the flow cell system using the peristaltic pump (2) to dry the system. Thereafter, the system was filled with a 0.3 mM glucose-containing FAB culture medium. 500 μL of a bacterial suspension was injected into the glass cell (4) from the upper surface, and the glass cell was sealed by turning off the three-way turncock (7a,7b). The cell as such was allowed to stand for 1 hour at room temperature. After the static culture, two of the three-way turncocks (7a,7b) were turned on, so as to supply each test liquid and control test liquid at a flow rate of 200 μL per minute. With a fluorescence confocal microscope, the process of biofilm formation (deposition) by the Pseudomonas aeruginosa (gfp expression PAO1-strain) adhered to the inner wall of the glass cell was observed three-dimensionally from above to observe changes over time (after 1 hour, 48 hours, 60 hours, 72 hours, and 84 hours). Note that the test liquid and the control test liquid were replaced with fresh liquids every 36 hours.

FIGS. 2 to 8 show comparison results between the biofilm condition in the experiments for the control test liquid (control test) and the biofilm condition in the experiments for the test liquids (Compounds 1a-1, 1b-1, 1c-1, 1c-2, 1d-1, or Comparative Compounds 1 to 3). FIGS. 2 to 8 show three-dimensional conditions of Pseudomonas aeruginosa (gfp expression PAO1-strain) adhered to the inner wall of the glass cell in the respective experiments, with the front views of the inner wall of the glass cell and the cross-sectional (vertical and horizontal) views of the glass cells.

According to those results, in the control test using the control test liquid, it was observed that Pseudomonas aeruginosa (gfp expression PAO1-strain) formed a huge, thick biofilm; however, in the test using a test liquid containing Compounds 1a-1, 1b-1, 1c-1, 1c-2, or 1d-1, such biofilm formation was not observed. Meanwhile, in the test using a test liquid containing Comparative Compounds 1, 2 or 3, the huge, thick biofilm was observed as in the control test. This showed that the Compounds 1a-1, 1b-1, 1c-1, 1c-2 and 1d-1 obtained in Production Examples 1, 3 and 5 to 7 are capable of inhibiting biofilm formation by Pseudomonas aeruginosa.

Experiment Example 2

Evaluation Test for Biofilm Formation Inhibition Effect Against Periodontitis Pathogenic Bacteria As with Experiment Example 1, using the flow cell system of FIG. 1, an inhibitory effect against biofilm formation by periodontitis pathogenic bacteria was evaluated for each of the amide compounds produced in Production Examples 1, 3, 5, and 6 (Compounds 1a-1, 1b-1, 1c-1, 1c-2).

Materials

Bacteria

Periodontitis pathogenic bacteria Porphyromonas gingivalis 381-strain (clinical strain) was used.

Culture Medium

A GAM culture medium containing hemin 5 μg/L and menadione 1 μg/L was used.

Bacterial Suspension

The 381-strain was inoculated in the GAM culture medium, and cultivated until stationary phase ($OD_{550}$=1.8). Then the culture medium was diluted 20-fold by a fresh GAM culture medium containing the above-mentioned substances.

Test Liquid and Control Test Liquid

Test Liquid

The test liquid was prepared by dissolving 100 μM of each of the Compounds 1a-1, 1b-1, 1c-1, or 1c-2 according to Production Examples 1, 3, 5 and 6 and 100 μM of Comparative Compounds 1 and 2 as comparative examples in dimethyl sulfoxide (DMSO), and supplying the resulting DMSO solutions to the above-mentioned bacterial suspensions so that the concentration of each compound becomes 0.1%(v/v).

Control Test Liquid

A DMSO not containing the compound was used as a control test liquid.

Test Method

The glass cell (4) of the flow cell system (see FIG. 1) was replaced with a stainless cell (3×7×120 mm), and 10 hydroxyapatite (HA) disks (6 mm in diameter, 1 mm in thickness) were placed in the cell. The HA disks had been subjected to salivary treatment overnight. Each of the test liquids and control test liquids was circulated in the system at a flow rate of 8 mL/min for 14 days. Note that the test liquids and the control test liquids were replaced with fresh liquids every two days.

After the cultivation, the HA disks were dipped in 300 μL of sterile distilled water, and treated by supersonic wave for 30 minutes at 4° C. The biofilms formed in the HA disks were peeled off and suspended in distilled water. Then, 100 μL of the suspension liquid was measured for the turbidity with an absorptiometer (C07500 colorimeter, product of Funakoshi) (measurement wavelength=550 nm).

A mean OD was found based on the resulting OD values, excluding the minimum and maximum values. Also, a mean value of the turbidities for the Control Test Liquids was found in the same manner as the control mean OD value. A biofilm formation inhibition rate (Inhibition Rate) was found by the following formula.

Biofilm Formation Inhibition Rate (%)={(Mean OD Value)/(Mean Comparison OD Value)}×100

Table 1 shows the values.

TABLE 1

| Compound | Mean OD Value | Mean Comparison OD Value | Biofilm Formation Inhibition Rate (%) |
|---|---|---|---|
| 1a-1 | 0.49 | 0.79 | 37.4 |
| 1b-1 | 0.32 | 0.39 | 19.1 |
| 1c-1 | 0.522 | 0.585 | 11.0 |
| 1c-2 | 0.041 | 0.34 | 87.8 |
| Comparative Compound 1 | 0.629 | 0.464 | −36.0 |
| Comparative Compound 2 | 0.719 | 0.483 | −49.0 |

According to the results, the examined Compounds 1a-1, 1b-1, 1c-1 and 1c-2 are capable of inhibiting biofilm formation caused by periodontitis pathogenic bacteria.

Experiment Example 3

Evaluation Test for Biofilm Removal Effect with Respect to *Pseudomonas aeruginosa*

With the flow cell system of FIG. 1, a removal effect against biofilms formed by *Pseudomonas aeruginosa* was evaluated for each of the amide compounds produced in Production Examples 1, 3, 5, and 6 (Compounds 1a-1, 1b-1, 1c-1, 1c-2), and for Comparative Compounds 1 to 3 as comparative examples.

The evaluation for biofilm removal effect was performed as follows. After cultivation of bacterias in the glass cell (4) of the flow cell system to grow a biofilm in the inner cell wall, a test liquid containing one of the amide compounds was applied to the biofilm. Then the condition of the biofilm was observed with a fluorescence confocal microscope (Leica TCS SP2).

Materials

Bacteria

As with Experiment Example 1, a gfp expression PAO1-strain was used.

At for the culture medium, the glucose-containing FAB culture medium, trace metal solution, and bacterial suspension as those of Experiment Example 1 were used.

Test Liquid and Control Test Liquid

Test Liquid

The test liquid was prepared by dissolving 100 μM of each of the Compounds 1a-1, 1b-1, 1c-1 and 1c-2 according to Production Examples 1, 3, 5 and 6 and 100 μM of Comparative Compounds 1 to 3 as comparative examples denoted by the following formula in dimethyl sulfoxide (DMSO), and supplying the resulting DMSO solutions to a 0.3 mM glucose-containing FAB culture medium so that the concentration of each compound becomes 0.1%(v/v).

Control Test Liquid

A DMSO not containing the compound was used as a control test liquid.

Test Method

The flow cell system was filled with hydrous ethanol (70 volume %), and was allowed to stand for at least 12 hours to sterilize the system. Then, air having been filtrated by a membrane filter (8a) was supplied into the flow cell system using the peristaltic pump (2) to dry the system. Thereafter, the system was filled with a 0.3 mM glucose-containing FAB culture medium. 500 μL of the bacterial suspension was injected into the glass cell (4) from the upper surface, and the glass cell was sealed by turning off the three-way turncock (7a,7b). The cell as such was allowed to stand for an hour at room temperature.

After the static culture, two of the three-way turncocks (7a,7b) were turned on, so as to supply each test liquid and control test liquid at a flow rate of 200 μL per minute. With a fluorescence confocal microscope, the process of biofilm formation (deposition) by the *Pseudomonas aeruginosa* (gfp expression PAO1-strain) adhered to the inner wall of the glass cell was observed three-dimensionally from above to observe changes over time (after 3 days, 4 days, 5 days, 6 days, 7 days, and 10 days). Note that the test liquid and the control test liquid were replaced with fresh liquids every 36 hours.

FIG. 9 shows a biofilm condition in the experiment for the control test liquid (control test). Each picture image in FIG. 9 shows three-dimensional conditions of biofilms formed by *Pseudomonas aeruginosa* (gfp expression PAO1-strain) adhered to the inner wall of the glass cell, with the front views of the inner wall of the glass cell and the cross-sectional (vertical and horizontal) views of the glass cells. FIGS. 10 to 13 show biofilm conditions in the experiments for different test liquids: Compounds 1a-1, 1b-1, 1c-1, and 1c-2, respectively. FIGS. 14 to 16 show biofilm conditions in the experiments for test liquids containing Comparative Compounds 1 to 3, respectively. According to those results, in the control test using the control test liquid, it was observed that *Pseudomonas aeruginosa* (gfp expression PAO1-strain) formed a huge, thick biofilm that further grew even larger after a ten-day cultivation. In contrast, in the test using the test liquid containing Compound 1a-1, 1b-1, 1c-1 or 1c-2, the gradual disappearance of the deposited biofilm with time was observed (FIGS. 10 to 13). Also, the gradual exfoliation of the deposited biofilm from the cell wall, and the flowing flakes of biofilm exfoliation in the cell were also visually observed. In the test liquids containing Compounds 1c-1 and 1c-2, the biofilm was first reduced and then increased again after a six-day cultivation, before it reduced again until it disappeared (FIGS. 12 and 13). This shows that biofilm formation and removal alternately occur. Meanwhile, in the test using the test liquids containing Comparative Compounds 1 to 3, such disappearance of biofilm was not observed (FIGS. 14 to 16). This result showed that Compounds 1a-1, 1b-1, 1c-1, and 1c-2 prepared in Production Examples 1, 3, 5 and 6 are effective for stripping off or removing deposited biofilms.

Experiment Example 4

Evaluation Test for Disinfecting Effect

The following test compounds were examined for the disinfecting activities against *Pseudomonas aeruginosa, E. Coli* and *staphylococcus aureus*, according to a broth dilution method of "CLSI (M7-A7) 2006" (Clinical and Laboratory Standards Institute, M7-A7, Methods for Dilution Antimicrobial Susceptibility Tests for Bacteria That Grow Aerobically; Approved Standard-Seventh Edition, 2006).
Test Compound
(1) Carbenicillin (CBPC),
(2) Ceftazidime (CAZ),
(3) Tobramycin (TOB),
(4) Azithromycin (AZM),
(5) Hydrochloride salt of Compound 1a-1 (Production Example 1)
(6) Hydrochloride salt of Compound 1a-2 (Production Example 2)
(7) Hydrochloride salt of Compound 1b-1 (Production Example 3)
(8) Hydrochloride salt of Compound 1b-2 (Production Example 4)
Note that, (1) to (4) are known antibiotics.
Bacteria Evaluated (Provided by Professor Dr. Suga from Tokyo University Research Center for Advanced Science and Technology)
 *Pseudomonas aeruginosa* PAO1
 *Pseudomonas aeruginosa* ATCC 27853
 *Escherichia coli* ATCC 25922
 *Staphylococcus aureus* ATCC 29213
 *Staphylococcus aureus* Methicillin resistant (MRSA) ATCC 43300
Test Method
Each of above-mentioned bacteria was inoculated in a TSB culture medium (Bacto TSB Broth, product of BD) for overnight cultivation at 37° C. The culture solution was applied to a TSB agar plate for about a 20-hour cultivation to form colonies. Three to five colonies were taken from the agar plate, and an average colony of them was inoculated in a 4 mL TSB culture medium. The colony was cultivated at 35° C. until the number of microorganisms became $1\times10^8$ to $2\times10^8$ CFU/mL. The number of microorganisms with time was found by measuring changes in absorbency at 590 nm of culture solution with time. When the turbidity became equivalent to 0.5 McFarland standard, it was determined that the number of microorganisms reached the target level=$1\times10^8$ to $2\times10^8$ CFU/mL.

The *bacillus* culture solution thus obtained was diluted 10-fold within 15 minutes, and a 5 μL portion was inoculated in each well of an evaluation 96-well microplate. This 96-well microplate was a sterilized 96-well microplate with U-shaped bottoms (Falcon 35-3918: product of BD), and each well was filled with a 100 μL portion of MH culture medium (BBL MH Broth: product of BD). Within 15 minutes after inoculation of the *bacillus* culture solutions, the test compounds were supplied to the well in a manner of 2-fold graded dilution. The cultivation was then carried out at 37° C. for 18 hours.

The MIC was determined as follows. "S (Susceptible)" indicates a concentration which caused 80% or more reduction in the diameter of the aggregation deposited in the bottom of the well, compared to when the test liquid is not used. "R (Resistant)" indicates a concentration that caused less than 80% reduction in diameter. The reduction was measured visually. "I (Intermediate)" indicates a concentration that cannot be measured visually.
Test Result Table 2 shows the measurements of disinfectant properties of the known compounds (1) to (4) (CBPC, CAZ, TOB, AZM). The right column of Table 2 shows published measurements of their disinfecting activities, according to the "CLSI (M100-S16) 2006" (Clinical and Laboratory Standards Institute, M100-S16, Performance Standards for Antimicrobial Susceptibility Testing; Sixteenth Informational Supplement, 2006) liquid dilution method.

TABLE 4

| | Test Result | | |
|---|---|---|---|
| MIC (μg/mL) | R | I | S |
| *P. aerugirrosa* PAO1 | | | |
| CBPC | ≤64 | — | ≥128 |
| CAZ | ≤0.5 | 1 | ≥2 |
| TOB | ≤0.25 | 0.5 | ≥1 |
| AZM | ≤32 | 64 | ≥128 |
| *P. aeruginosa* ATCC 27853 | | | |
| CBPC | ≤64 | 128 | ≥256 |
| CAZ | ≤1 | 2 | ≥4 |
| TOB | ≤0.25 | 0.5 | ≥1 |
| AZM | ≤32 | 64 | ≥128 |
| *E. coli* ATCC 25922 | | | |
| CBPC | ≤8 | 16 | ≥32 |
| CAZ | ≤0.063 | 0.125 | ≥0.25 |
| TOB | ≤0.25 | 0.5 | ≥1 |
| AZM | ≤2 | 4 | ≥8 |
| *S. aureus* ATCC 29213 | | | |
| CBPC | ≤8 | — | ≥16 |
| CAZ | ≤2 | 4 | ≥8 |
| TOB | ≤0.125 | 0.25 | ≥0.5 |
| AZM | ≤0.5 | 1 | ≥2 |
| MRSA ATCC 43300 | | | |
| CBPC | ≤16 | 32 | ≥64 |
| CAZ | ≤4 | 8 | ≥16 |
| TOB | ≤64 | 128 | ≥256 |
| AZM | ≤1024 | — | — |

TABLE 4-continued

| Publicly-known data MIC (µg/mL) from M100-S16 | |
|---|---|
| *P. aeruginosa* ATCC 27853 | |
| CBPC | none |
| CAZ | 1-4 |
| TOB | 0.25-1 |
| AZM | none |
| *E. coli* ATCC 25922 | |
| CBPC | none |
| CAZ | 0.06-0.5 |
| TOB | 0.25-1 |
| AZM | none |
| *S. aureus* ATCC 29213 | |
| CBPC | none |
| CAZ | 4-16 |
| TOB | 0.12-1 |
| AZM | 0.5-2 |

Because this data is consistent with the data given by the above test, it was confirmed that the above test properly evaluated the disinfecting activities of Compounds (1) to (4).

Table 3 shows the result for each hydrochloride of Compounds 1a-1, 1a-2, 1b-1 and 1b-2 of the present invention.

| MIC (µg/mL) | R | I | S |
|---|---|---|---|
| Hydrochloride salt of Compound 1a-1 | | | |
| *P. aeruginosa* PAO1 | ≤32 | 64 | ≥128 |
| *P. aeruginosa* ATCC 27853 | ≤32 | 64 | ≥128 |
| *E. coil* ATCC 25922 | ≤4 | 8 | ≥16 |
| *S. aureus* ATCC 29213 | ≤4 | 8 | ≥16 |
| MRSA ATCC 43300 | ≤4 | 8 | ≥16 |
| Hydrochloride salt of Compound 1a-2 | | | |
| *P. aeruginosa* PAO1 | ≤512 | — | ≥1024 |
| *P. aeruginosa* ATCC 27853 | ≤512 | — | ≥1024 |
| *E. coil* ATCC 25922 | ≤128 | — | ≥256 |
| *S. aureus* ATCC 29213 | ≤128 | — | ≥256 |
| MRSA ATCC 43300 | ≤128 | — | ≥256 |
| Hydrochloride salt of Compound 1b-1 | | | |
| *P. aeruginosa* PAO1 | ≤32 | 64 | ≥128 |
| *P. aeruginosa* ATCC 27853 | ≤32 | 64 | ≥128 |
| *E. coil* ATCC 25922 | ≤8 | — | ≥16 |
| *S. aureus* ATCC 29213 | ≤4 | 8 | ≥16 |
| MRSA ATCC 43300 | ≤4 | 8 | ≥16 |
| Hydrochloride salt of Compound 1b-2 | | | |
| *P. aeruginosa* PAO1 | ≤512 | — | ≥1024 |
| *P. aeruginosa* ATCC 27853 | ≤512 | — | ≥1024 |
| *E. coil* ATCC 25922 | ≤128 | — | ≥256 |
| *S. aureus* ATCC 29213 | ≤128 | — | ≥256 |
| MRSA ATCC 43300 | ≤128 | — | ≥256 |

According to Table 3, those compounds have disinfecting activities comparative to that of existing antibiotics.

EFFECT OF THE INVENTION

The compound of the present invention is capable of inhibiting biofilm formation and removing formed biofilms, thereby solving various defects caused by biofilms formed by microorganisms.

With the particular characteristic of inhibiting biofilm formation by periodontitis pathogenic bacteria or *Pseudomonas aeruginosa* and also stripping off or removing the already-formed biofilms, the compound of the present invention is useful for various purposes. The compound of the present invention is also effective for treating intractable biofilm infections. With this characteristic, the compound of the present invention will greatly contribute to a complete cure of the biofilm infections.

For example, *Pseudomonas aeruginosa*, which exists everywhere in the natural environment, requires a small amount of organic matter and moisture to breed and grow into a biofilm. Therefore, *Pseudomonas aeruginosa* often causes in-hospital infections, substituted microbism, opportunistic infection, and sanitary defects in water pipes or water storage tanks.

Further, periodontitis pathogenic bacteria forms a biofilm called plaque, which causes oral odor or intraoral diseases such as periodontitis or alveolar pyorrhea. It has been publicly known that the removal of plaque is important in intraoral sanitation or for the treatment of intraoral diseases. However, as described above, biofilms are resistant to drugs such as disinfectants to a certain extent.

In view of this problem, the biofilm remover or biofilm formation inhibitor of the present invention inhibits biofilms formation by *Pseudomonas aeruginosa* in pipes or water storage tanks in hospital facilities or private residences, and also facilitates removal of deposited biofilms, thereby preventing in-hospital infections or other various defects caused by biofilms and improving environmental sanitation. The biofilm remover or biofilm formation inhibitor of the present invention is also capable of inhibiting biofilm formation by periodontitis pathogenic bacteria and removing biofilms formed by periodontitis pathogenic bacteria, found on teeth, gingiva or intraoral dental materials, thereby effectively preventing or treating gingival disease such as periodontitis or alveolar pyorrhea, intraoral diseases such as stomatitis, as well as reducing oral odor.

The compound of the present invention, particularly a compound denoted by General Formula (1) containing a substituent Q denoted by Formula (Q1) or a salt thereof, has excellent disinfecting activity with respect to many kinds of bacteria including *Pseudomonas aeruginosa*, *E. Coli*, and *staphylococcus aureus*. The compound is therefore useful for disinfectants.

The invention claimed is:

1. An amide compound denoted by General Formula (1) or salt thereof:

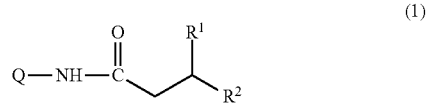

(1)

wherein $R^1$ is a hydrogen atom or a hydroxyl group, $R^2$ is a $C_{5-12}$ alkyl group, and Q is a substituent denoted by Formula (Q1) or (Q2),

(Q1)

(Q2)

wherein n and m are 0.

2. An amide compound or salt thereof according to claim 1, wherein, in General Formula (1), Q is a substituent denoted by Formula (Q1) wherein m is 0.

3. An amide compound or salt thereof according to claim 1, wherein, in General Formula (1), Q is a substituent denoted by Formula (Q2) wherein n is 0.

4. An amide compound or salt thereof according to claim 1, wherein the amide compound denoted by General Formula (1) is at least one compound selected from the group consisting of:
N-(pyrrolidin-3-yl) decanoyl amide,
N-(pyrrolidin-3-yl) dodecanoyl amide,
N-(pyrrolidin-1-yl) dodecanoyl amide, and
N-(pyrrolidin-1-yl)-3-hydroxy dodecanoyl amide.

5. A biofilm remover containing the amide compound or salt thereof according to claim 1, as an active ingredient.

6. A biofilm remover according to claim 5, wherein the biofilm is film formed by *Pseudomonas aeruginosa* or periodontitis pathogenic bacteria.

7. A biofilm formation inhibitor containing the amide compound or salt thereof according to claim 1, as an active ingredient.

8. A biofilm formation inhibitor according to claim 7, wherein the biofilm is film formed by *Pseudomonas aeruginosa* or periodontitis pathogenic bacteria.

9. A disinfectant containing the amide compound or salt thereof according to claim 1, as an active ingredient.

10. A disinfectant according to claim 9, wherein the amide compound is denoted by General Formula (1) wherein Q is a substituent denoted by Formula (Q1) wherein m is 0.

11. A disinfectant according to claim 9, wherein the amide compound is at least one compound selected from the group consisting of:
N-(pyrrolidin-3-yl) decanoyl amide,
N-(pyrrolidin-3-yl) dodecanoyl amide,
N-(pyrrolidin-4-yl) decanoyl amide, and
N-(pyrrolidin-4-yl) dodecanoyl amide.

12. An oral composition containing the biofilm remover according to claim 6 for removing biofilms formed by periodontitis pathogenic bacteria, the biofilm formation inhibitor according to claim 8 for inhibiting biofilms formed by periodontitis pathogenic bacteria, or the disinfectant according to claim 9.

* * * * *